(12) United States Patent
Cabiri

(10) Patent No.: US 10,286,151 B2
(45) Date of Patent: May 14, 2019

(54) PLUNGER WITH REDUCED LEAKAGE DURING STORAGE

(71) Applicant: MEDIMOP Medical Projects Ltd., Ra'anana (IL)

(72) Inventor: Oz Cabiri, Macabim-Reut (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 15/054,990

(22) Filed: Feb. 26, 2016

(65) Prior Publication Data

US 2017/0246394 A1     Aug. 31, 2017

(51) Int. Cl.
  *A61M 5/315*    (2006.01)
  *A61M 5/31*     (2006.01)
  *B65B 3/00*     (2006.01)
  *B65B 3/04*     (2006.01)

(52) U.S. Cl.
  CPC .......... *A61M 5/31* (2013.01); *A61M 5/31513* (2013.01); *A61M 5/31515* (2013.01); *B65B 3/003* (2013.01); *B65B 3/04* (2013.01); *A61M 2005/3101* (2013.01)

(58) Field of Classification Search
  CPC ...... A61M 5/31513; A61M 2005/3101; A61M 2005/31521
  See application file for complete search history.

(56) References Cited

U.S. PATENT DOCUMENTS

| | | |
|---|---|---|
| 2,895,773 A | 7/1959 | McConnaughey |
| 4,543,093 A | 9/1985 | Christinger |
| 5,411,489 A | 5/1995 | Pagay et al. |
| 5,735,825 A * | 4/1998 | Stevens ............. A61M 5/31513 604/218 |
| 6,090,081 A | 7/2000 | Sudo et al. |
| 8,038,656 B2 | 10/2011 | Lloyd et al. |
| 2005/0154353 A1 | 7/2005 | Alheidt |

(Continued)

FOREIGN PATENT DOCUMENTS

| | | |
|---|---|---|
| WO | 1995030444 A1 | 11/1995 |
| WO | 2015054282 A2 | 4/2015 |

OTHER PUBLICATIONS

Extended European Search Report dated Dec. 22, 2017 in EP Application 17157902.2.

*Primary Examiner* — Nathan R Price
*Assistant Examiner* — Tasnim Mehjabin Ahmed
(74) *Attorney, Agent, or Firm* — Panitch Schwarze Belisario & Nadel LLP

(57) ABSTRACT

A plunger seal for a drug delivery device may have a mobile and an enhanced sealing parked state. Optionally, the cartridge is stored with the plunger seal in the parked state. Optionally, drug discharge occurs with the plunger seal in the mobile state. For example in the parked state there may be increased normal force between the plunger seal and an inner wall of the cartridge. Optionally there is limited deformation of the plunger seal between the parked and mobile states. Optionally the plunger seal is biased to the parked state. Optionally, a distal force switches the plunger seal to the mobile state. For example, the plunger seal may have an inner cavity that is expanded radially by core. A biasing element optionally biases the core wedging it proximally to the parked state. A distal force on the core may push it distally to the mobile state.

5 Claims, 18 Drawing Sheets

(56) References Cited

U.S. PATENT DOCUMENTS

| | | |
|---|---|---|
| 2007/0003584 A1 | 1/2007 | Anderson |
| 2010/0264139 A1 | 10/2010 | Kawachi |
| 2011/0034882 A1 | 2/2011 | Quinn et al. |
| 2011/0137263 A1 | 6/2011 | Ashmead et al. |
| 2013/0060203 A1 | 3/2013 | Svensson |
| 2014/0207081 A1 | 7/2014 | Quinn et al. |
| 2017/0296756 A1* | 10/2017 | Giraud .............. A61M 5/31578 |

* cited by examiner

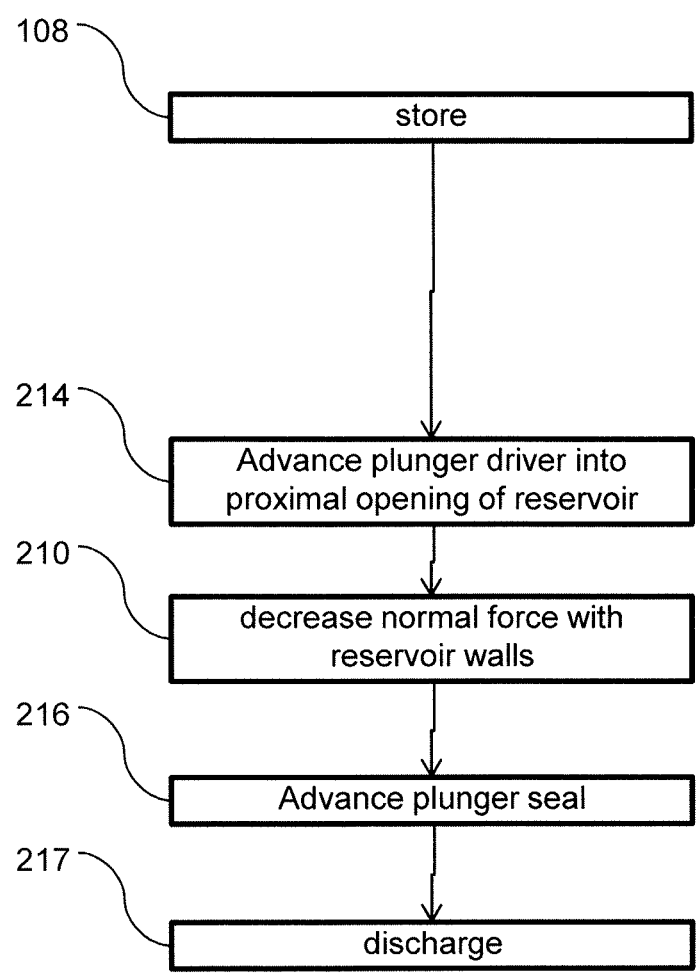

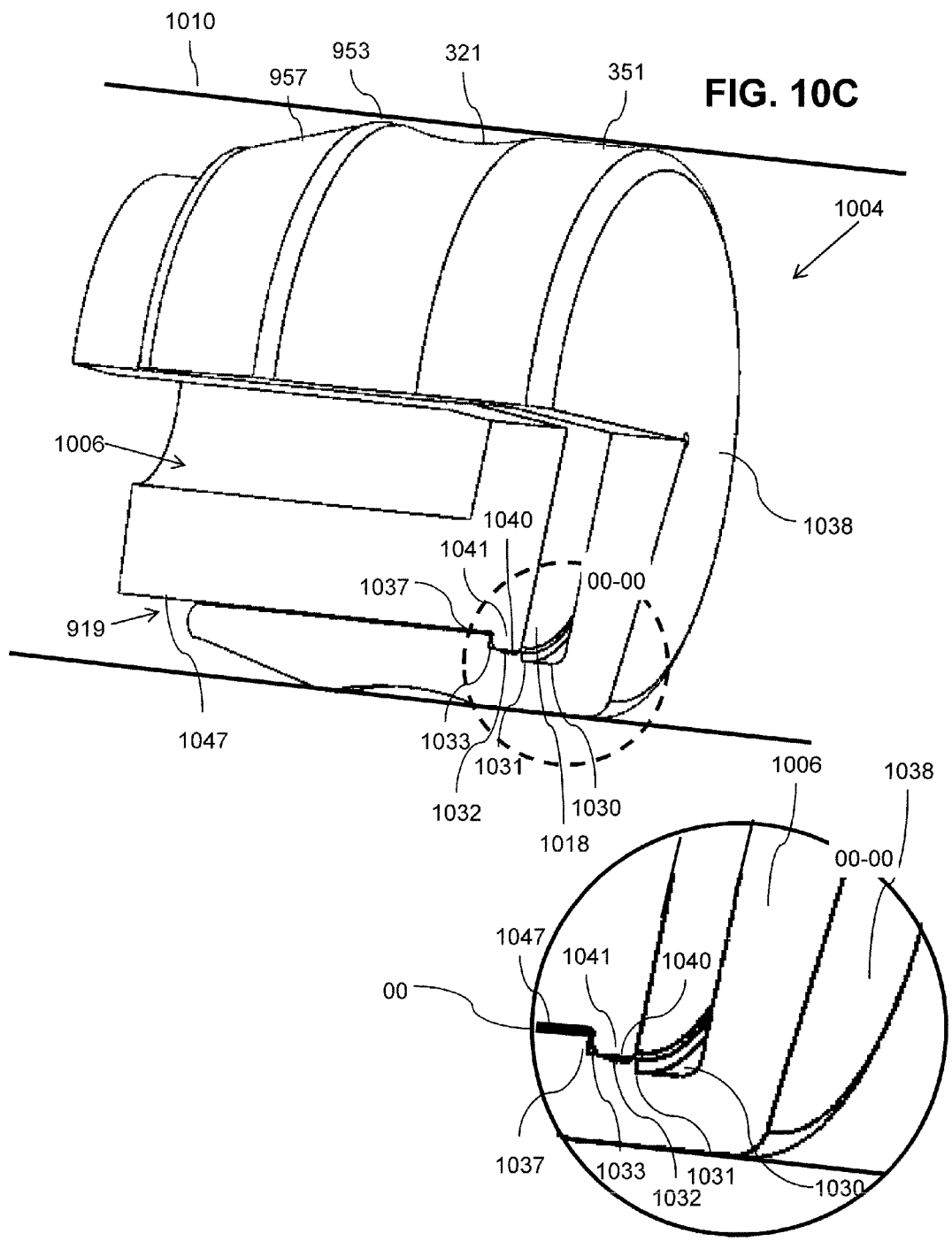

PLUNGER WITH REDUCED LEAKAGE DURING STORAGE

FIELD AND BACKGROUND OF THE INVENTION

The present invention, in some embodiments thereof, relates to a plunger seal for a medicine cartridge (e.g. a syringe) and, more particularly, but not exclusively, to a plunger seal with adjustable sealing force against an inner wall of the syringe.

U.S. Pat. No. 5,411,489 discloses "pre-filled syringes equipped with an improved plunger, a plunger actuating cylinder and a plunger rod, characterized by a leak-proof seal and easy sliding property".

U.S. Pat. No. 6,090,081 discloses "a sealing stopper for a syringe, having very high sealing property and sliding property, and a prefilled syringe using this sealing stopper and capable of preserving a medicament for a long time and operating in easy and precise manner during injecting. This syringe is also excellent in sanitary and operating property during a step of formulation or preservation of a medicament. In this sealing stopper for a syringe, a surface of the rubber body is laminated with a tetrafluoroethylene resin film or ultra-high molecular weight polyethylene film having an average roughness Ra on the central line of the surface in a range of at most 0.05 μm and a kinematic friction coefficient of at most 0.2."

International Patent Application Publication no. 1995/030444 discloses, "A syringe comprising a barrel, a plunger and a plunger rod. The plunger can be deformed by the plunger rod to draw the radial walls of the plunger away from the inner wall of the barrel and thus reduce the friction between the plunger and the barrel, to facilitate injection. The deformation can also be used to aspirate the syringe. The invention also provides a method of delivering a liquid medium into a patient using such a syringe."

U.S. Pat. No. 2,895,773 discloses "a piston having a piston head on which is mounted an elastic cap having one and preferably at least two rings joined by a web.

The rings are arranged to roll about shoulders formed on the piston head. The material of the piston cap may be stretched both longitudinally and radially." and that "the principles of the invention . . . are illustrated with respect to hypodermic syringes", but, "that the invention will function with equal effectiveness in any device in which a piston having sealing rings of elastic material can be used".

U.S. Pat. No. 4,543,093 discloses "A plunger rod assembly for use with a syringe barrel," comprising, "a plunger rod and a flexible thermoplastic stopper. A plunger rod includes an elongate shaft portion defining a longitudinal axis and having a tapered tip portion at the distal end thereof. The tapered tip portion includes a front portion at the distal end thereof and a circular tapered plunger rod wall connected to the front portion and having a convexly shaped surface. A flexible cup-shaped thermoplastic stopper includes an annular side wall and a continuous front wall connected to the side wall. An exterior surface of the side wall is larger in diameter than the syringe barrel inside diameter. The stopper interior includes an inside surface of the front wall and a tapered annular inside wall connected to the annular side wall and to the inside surface. The tapered annular inside wall and the inside surface define a cavity which has the tapered tip portion received therein. The tapered annular inside wall is inclined in the same direction as the tapered plunger rod wall and adjacent thereto. Cooperating structure for maintaining the positional relationship of the stopper and the plunger rod is also provided".

Additional background art includes U.S. Pat. No. 8,038,656, US Patent Publication Application no. 2013/0060203, US Patent Publication Application no. 2007/0003584, US Patent Publication Application no. 2011/0137263, and US Patent Publication Application no. 2010/0264139. Eakins, Minn. (2009) Advances in formation, filling and inspection of prefilled syringes suitable for sensitive biopharmaceuticals. Pharmaceutical Outsourcing 10(7): 24-28. Eakins, Minn. (2010) plastic prefillable syringes and vials: Progress toward a wider acceptance. Pharmaceutical Outsourcing 11(1): 10-14. Lloyd Waxman, Harold Murray and Vinod Vilivalam, West Pharmaceutical Services, Inc., Lionville, Pa., Evaluation of piston movement and container integrity under severe storage conditions in plastic and glass prefilled syringes.

SUMMARY OF THE INVENTION

According to an aspect of a first embodiment of the invention, there is provided a method of packaging a drug in a reservoir the reservoir including a cylindrical bore with a distal opening and a proximal opening, the cylindrical bore prefilled in a distal portion thereof with the drug, the method comprising:

providing a plunger seal inserted into the bore in a first state wherein an external surface of the plunger seal includes a sealing region;

moving the plunger seal distally in the bore while the plunger seal is in the first state from outside the bore to a sealing position in the bore between the drug and the proximal opening;

switching the plunger seal to a parked state in the sealing position, the parked state having an increased normal force between the sealing region and an inner surface of the cylindrical bore of the reservoir the increased normal force resulting an increase in friction resistance to longitudinal movement of the plunger seal against the inner wall of the reservoir of at least 30% with respect to the first state and wherein a distortion in the shape of the sealing region between the first state and the parked state is less than 0.2 mm.

According to a second embodiment of the invention and optionally the first embodiment, a distortion in the shape of the sealing region between the first state and the parked state is less than 0.2 mm.

According to a third embodiment of the invention and optionally any of the first to the second in an unstressed state an outer width of the sealing region is less than 0.4 mm greater than an inner width of the cylindrical bore.

According to a third embodiment of the invention and optionally any of the first to the second embodiment, a maximum distortion on an exterior surface of the plunger seal between the first state and parked state in less than 0.4 mm.

According to a fourth embodiment of the invention and optionally any of the first to the third embodiment, a maximum distortion on a region of the outer surface of the plunger seal in contact with the drug between the first state and parked state in less than 0.4 mm.

According to a fifth embodiment of the invention and optionally any of the first to the fourth embodiment, the plunger seal includes a cavity having a proximal opening and further comprising: supplying a core shaped to fill at least a portion of the cavity; expanding an inner diameter of the cavity with the core to cause the increased normal force.

According to a sixth embodiment of the invention and optionally to the fifth embodiment, the plunger seal and the core fit entirely inside the cylindrical bore.

According to a seventh embodiment of the invention and optionally any of the fifth to the sixth embodiment, the core protrudes less than 2 cm from the proximal opening of the cavity.

According to an eighth embodiment of the invention and optionally any of the fifth to the seventh embodiment, the expanding is by introducing the core into the cavity subsequent to the moving.

According to a ninth embodiment of the invention and optionally eighth embodiment, the method further comprises: sealing the distal opening of the reservoir prior to the introducing.

According to a tenth embodiment of the invention and optionally any of the fifth to the ninth embodiment, the expanding, is by wedging the core into the cavity in a proximal directed wedging direction.

According to a eleventh embodiment of the invention and optionally the tenth embodiment, an angle of attack of the wedging is less than 15 degrees.

According to a twelfth embodiment of the invention and optionally any of the first to the eleventh embodiment, a force to drive the plunger driver distally into the reservoir in the first state is less than 400 g.

According to a thirteenth embodiment of the invention and optionally any of the first to the twelfth embodiment, a force to drive the plunger driver distally into the reservoir in the parked state is greater than 500 g.

According to a fourteenth embodiment of the invention and optionally any of the first to the thirteenth embodiment, the method further comprises: storing the drug in the reservoir subsequent to the increasing for at least twenty four hours.

According to a fifteenth embodiment of the invention and optionally any of the first to the fourteenth embodiment, the plunger seal has a preinserted state and wherein a maximum outer diameter of plunger seal is some preinserted state, ranges between 99% to 103% of inner diameter of the bore.

According to a sixteenth embodiment of the invention and optionally any of the tenth to the fifteenth embodiment, the method further comprises: retaining the core wedged into the cavity with a retaining force.

According to a seventeenth embodiment of the invention and optionally the sixteenth embodiment, the retaining force includes a proximally directed force of the plunger seal on the core.

According to a eighteenth embodiment of the invention and optionally any of the fifth to the seventeenth embodiment, the method further comprises: storing the drug in the reservoir with the core in the plunger seal in the sealing position for at least twenty four hours; inserting a plunger into the proximal cylindrical bore of the reservoir after the storing; reducing the normal force between the outer edge of the plunger seal and the inner surface of the reservoir by pushing the core distally with the plunger; advancing the plunger seal distally into the cylindrical bore thereby discharging the drug from the distal opening of the reservoir subsequent to the reducing the normal force.

According to a nineteenth embodiment of the invention and optionally any of the first to the eighteenth embodiment, the method further comprises: coating the outer edge of the plunger seal with a low friction coating.

According to a twentieth embodiment of the invention and optionally any of the first to the nineteenth embodiment, the method further comprises: compressing the plunger seal to increase the normal force.

According to a twenty first embodiment of the invention and optionally any of the first to the twentieth embodiment, the plunger is stable in the mobile state.

According to an aspect of a twenty second embodiment of the invention, there is provided a method of distributing a drug from a reservoir having a distal opening and a proximal opening, the reservoir prefilled in a distal portion thereof with the drug, the method comprising: providing a plunger parked state in a prefilled reservoir the plunger seal dividing between the drug in a distal portion of the reservoir and a proximal opening of the reservoir; pushing the plunger distally to switch the plunger into a mobile state having reduced radial force between the plunger seal and an inner wall of the reservoir while a maximum distortion region of a surface of the plunger seal in contact with the drug is less than 0.5 mm. further pushing the plunger proximally to discharge the drug from the distal opening of the reservoir subsequent with the plunger in the mobile state.

According to an aspect of a twenty third embodiment of the invention, there is provided a cartridge for a drug delivery device comprising: a reservoir including a longitudinally oriented cylindrical bore having a proximal opening; a plunger seal having a sealing region on an exterior surface thereof, the sealing region sized to fit closely into the cylindrical bore; the plunger seal including a cavity; a core fitting into the cavity and shaped to apply an outward force radially against an inner wall of the cavity thereby increasing a normal force between the sealing region and an interior wall of the cylindrical bore while a maximum deformation of the sealing region remains less than 0.5 mm.

According to a twenty fourth embodiment of the invention and optionally the twenty third embodiment, the core and the cavity are shaped such that applying a distal force to the core reduces the outward force.

According to a twenty fifth embodiment of the invention and optionally the twenty fourth embodiment, the core includes an interference element with a distally increasing radius and wherein the cavity includes a region with distally increasing radius.

According to a twenty sixth embodiment of the invention and optionally any of the twenty third to the twenty fifth embodiment, the core has a length less than 2 cm.

According to a twenty seventh embodiment of the invention and optionally any of the third to the second embodiment, an unstressed outer diameter of the sealing region ranges between 99 to 103% an inner diameter of the cylindrical bore.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

In this regard, the description taken with the drawings makes apparent to those skilled in the art how embodiments of the invention may be practiced.

In the drawings:

FIG. 1 is a flow chart illustration of a method of sealing a drug reservoir in accordance with an embodiment of the current invention;

FIG. 2 is a flow chart illustration of a method of discharging a drug from a cartridge in accordance with an embodiment of the current invention;

Figure 3A:
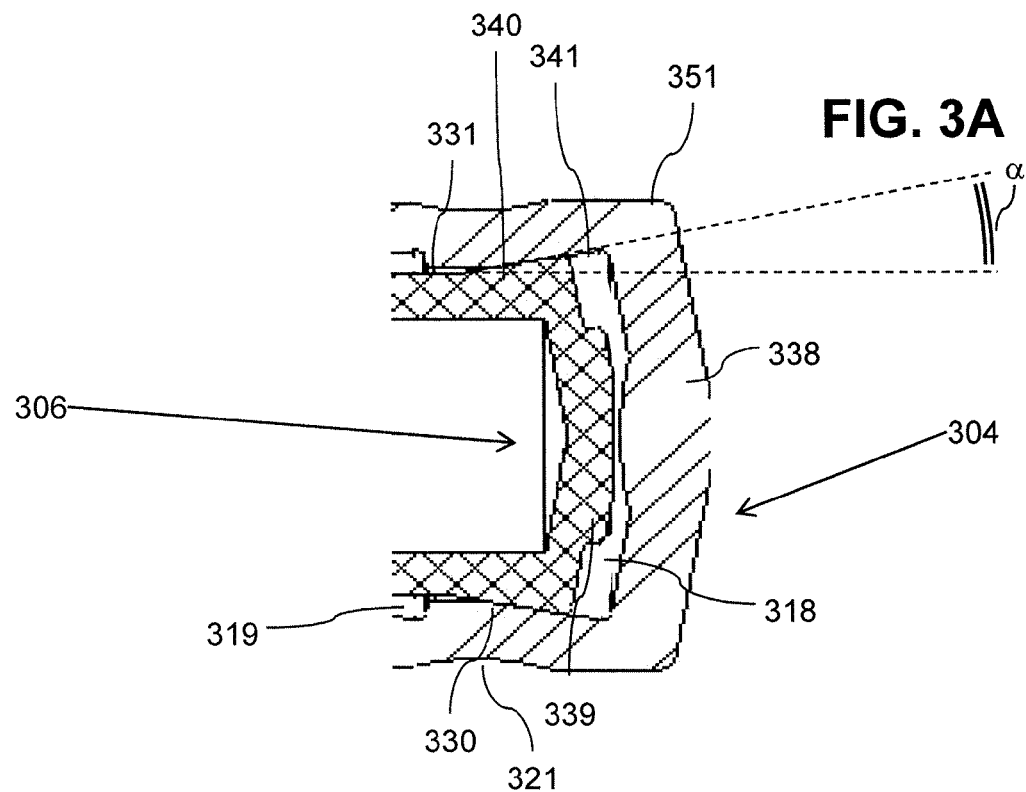
Figure 3B:
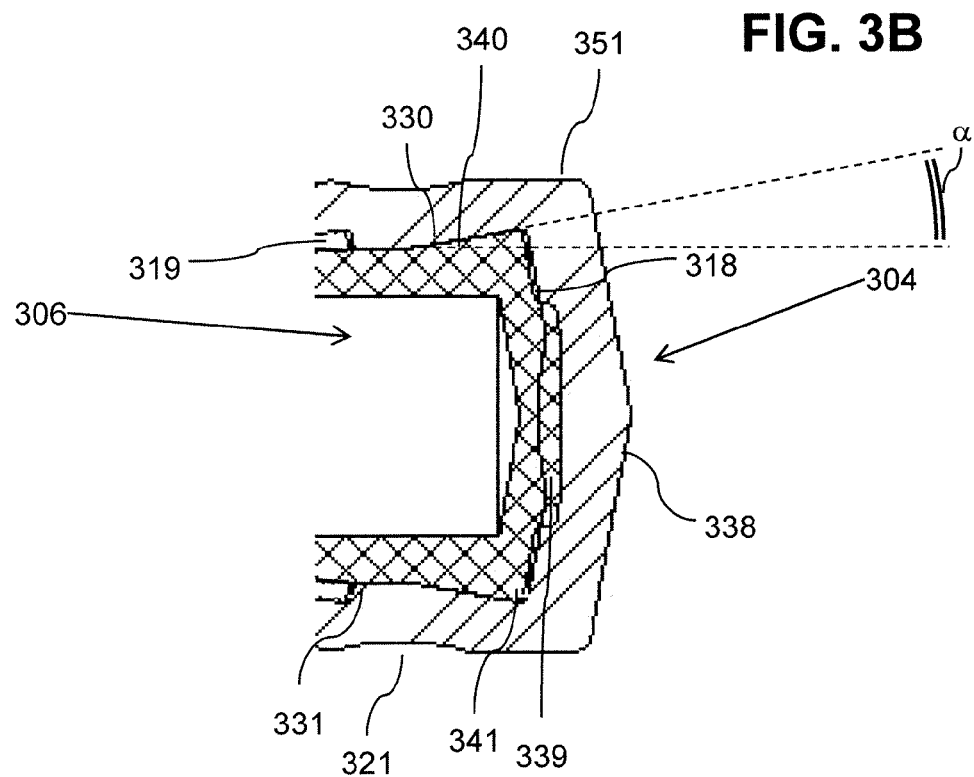
Figure 4:
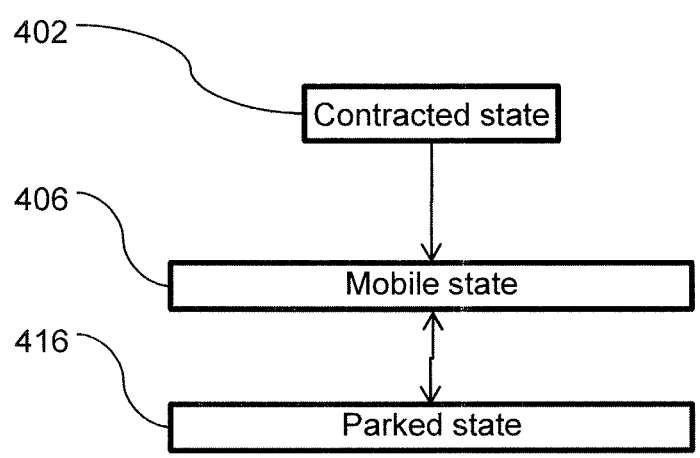
Figure 5A:
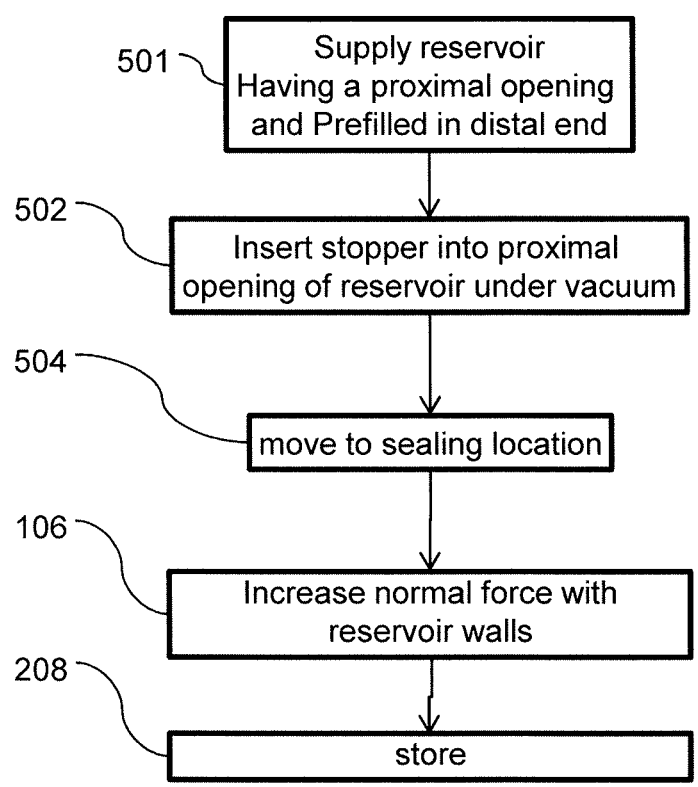
Figure 5B:
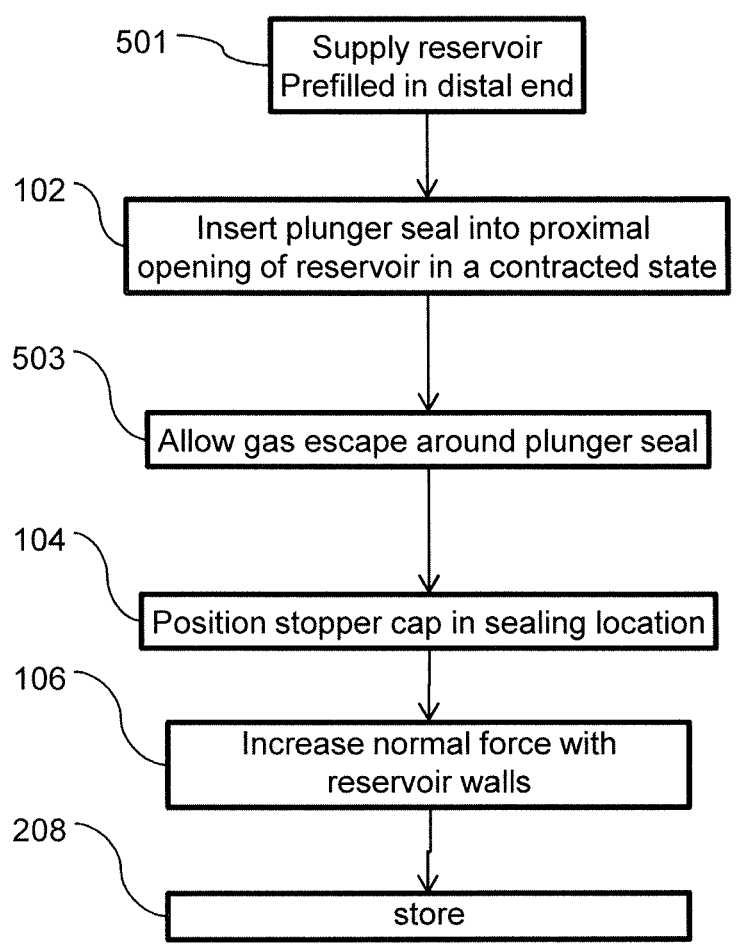
Figure 6:
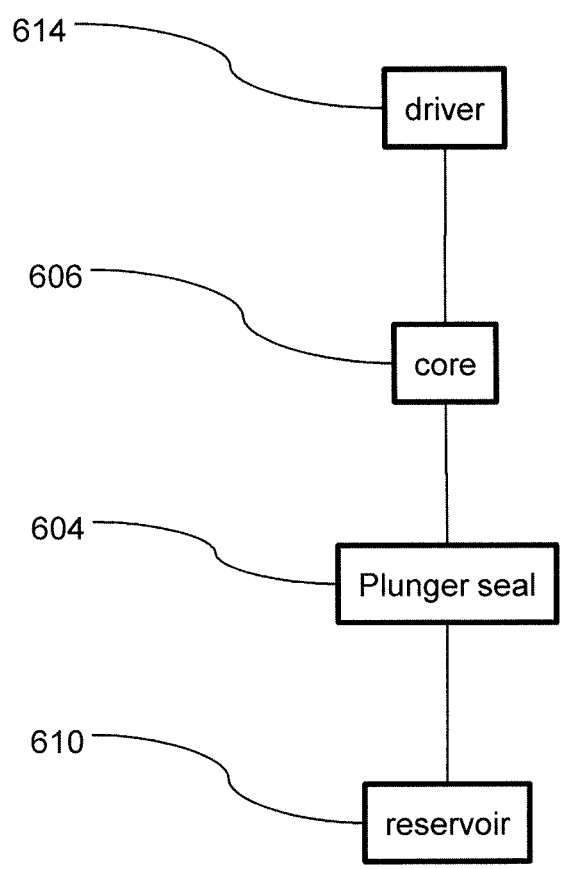
Figure 7:
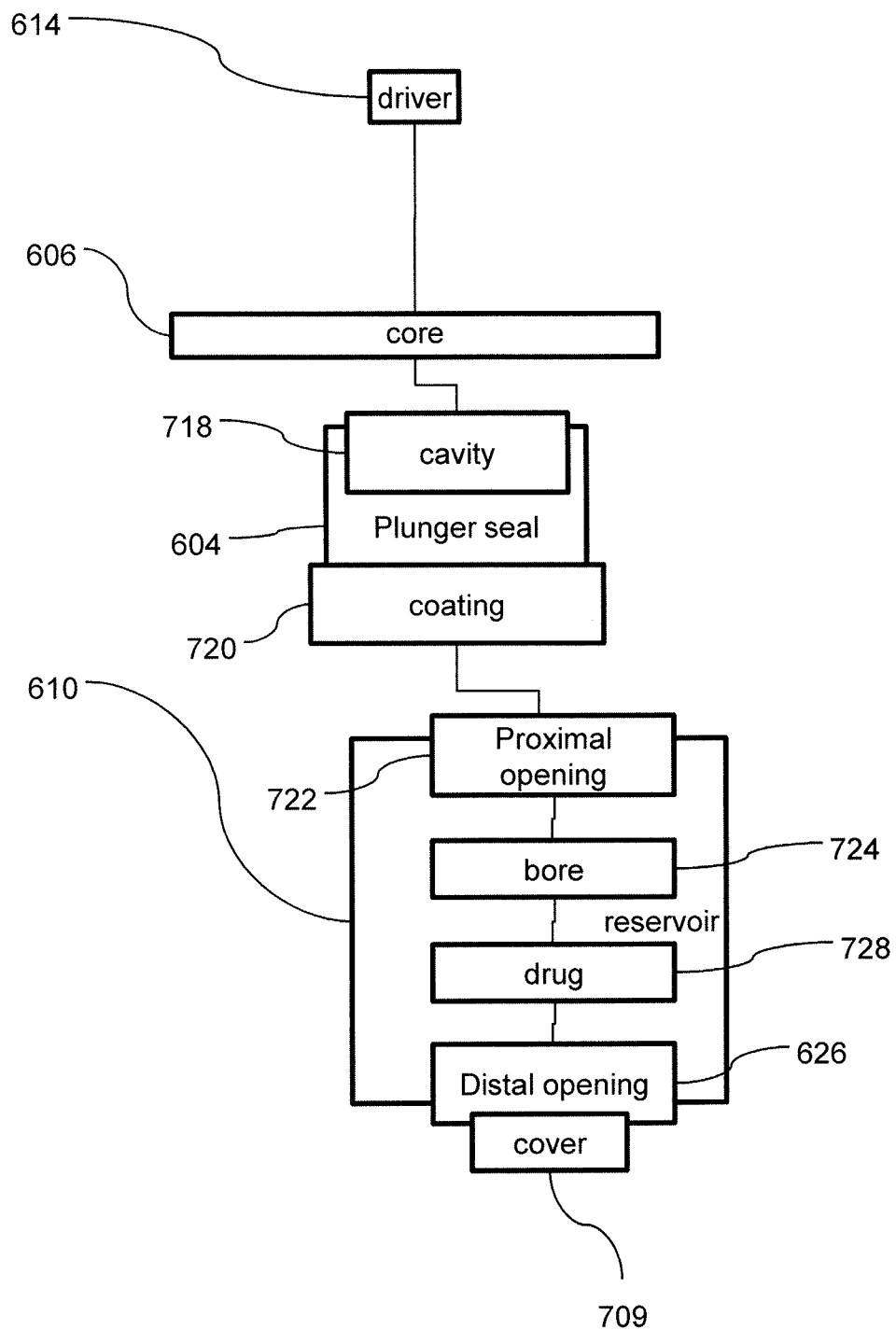
Figure 8A:
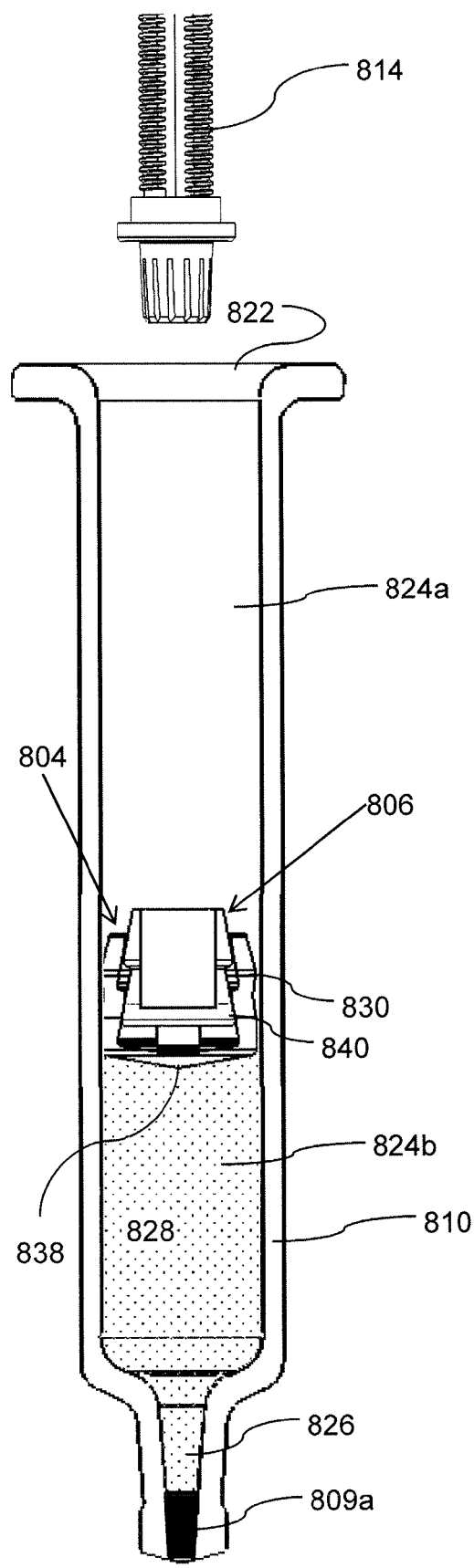
Figure 8B:
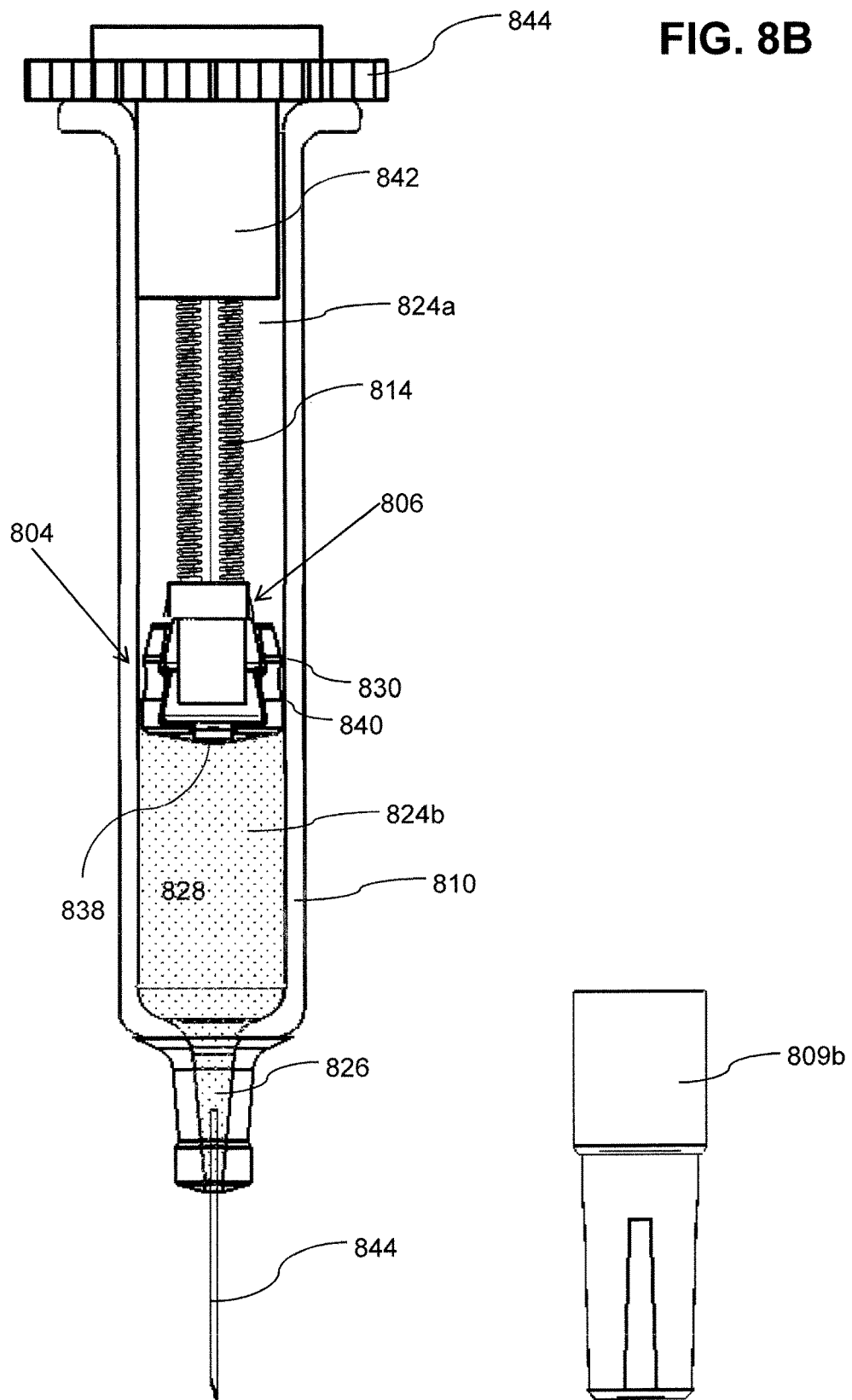
Figure 9A:
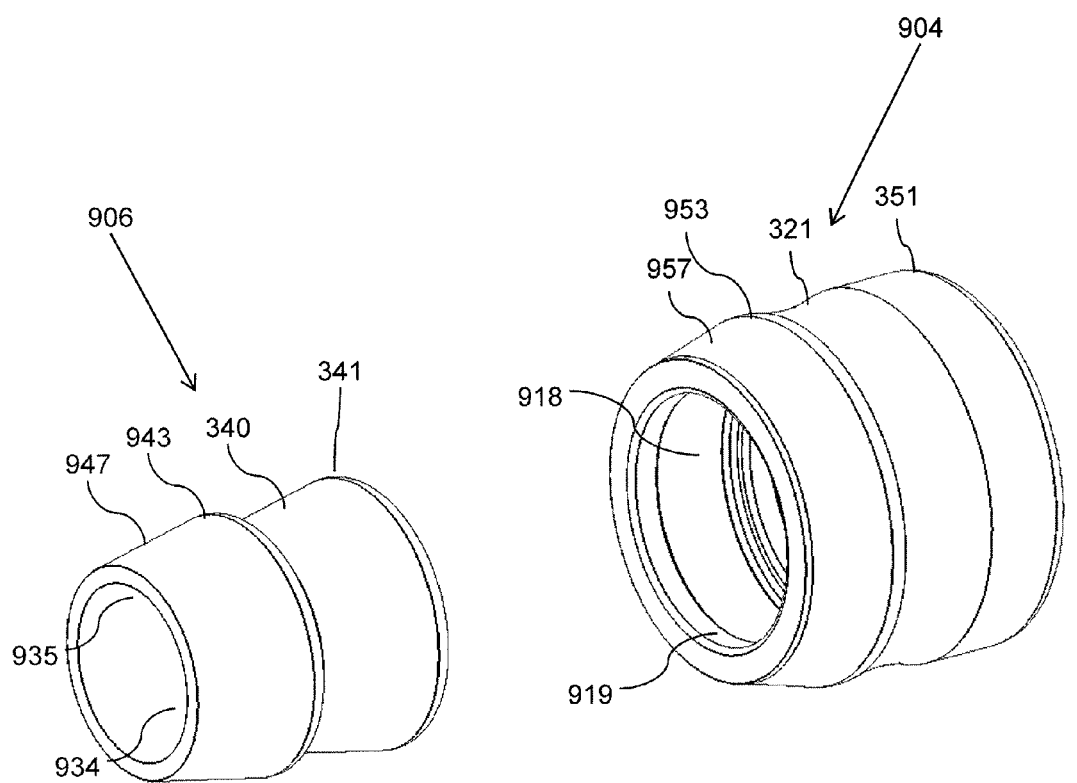
Figure 9B:
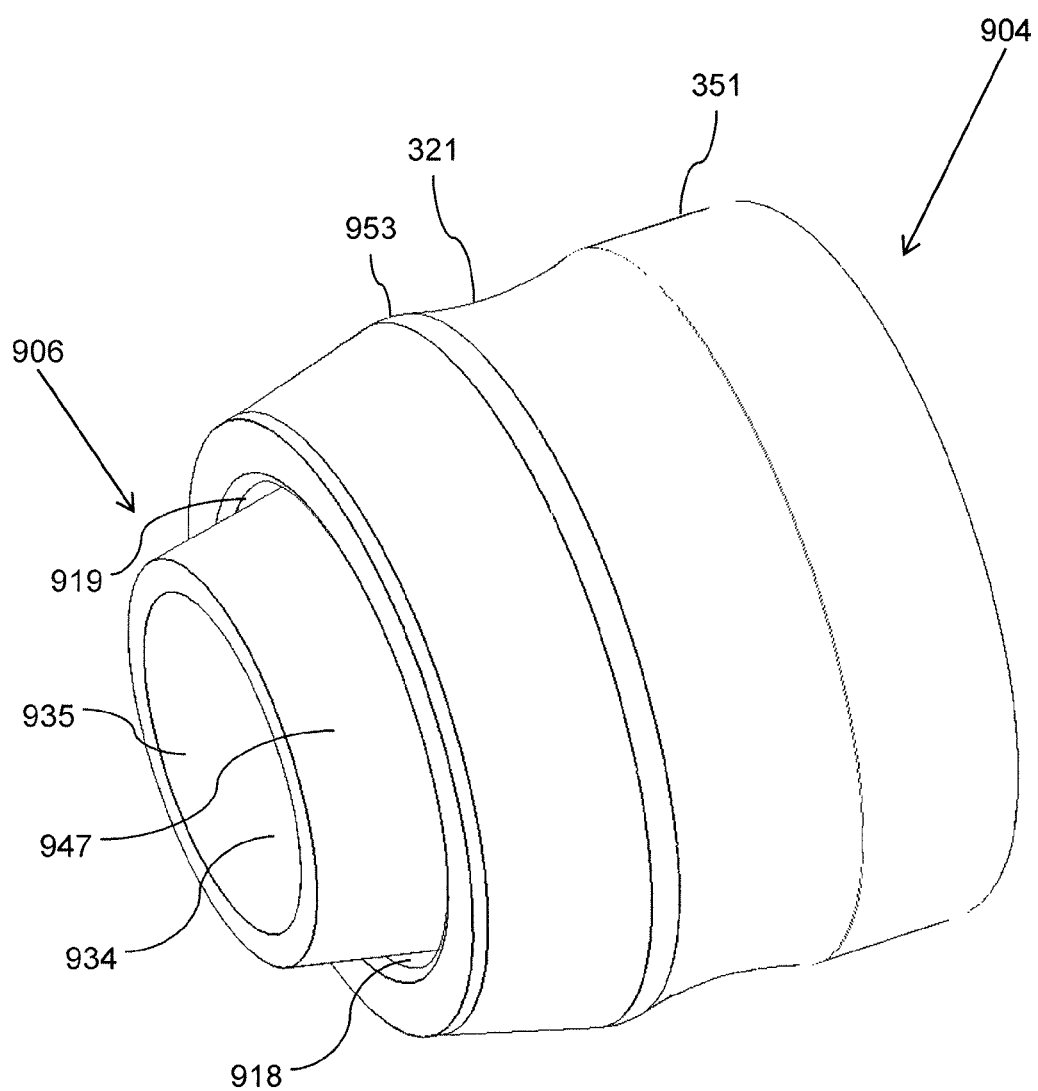
Figure 9C:
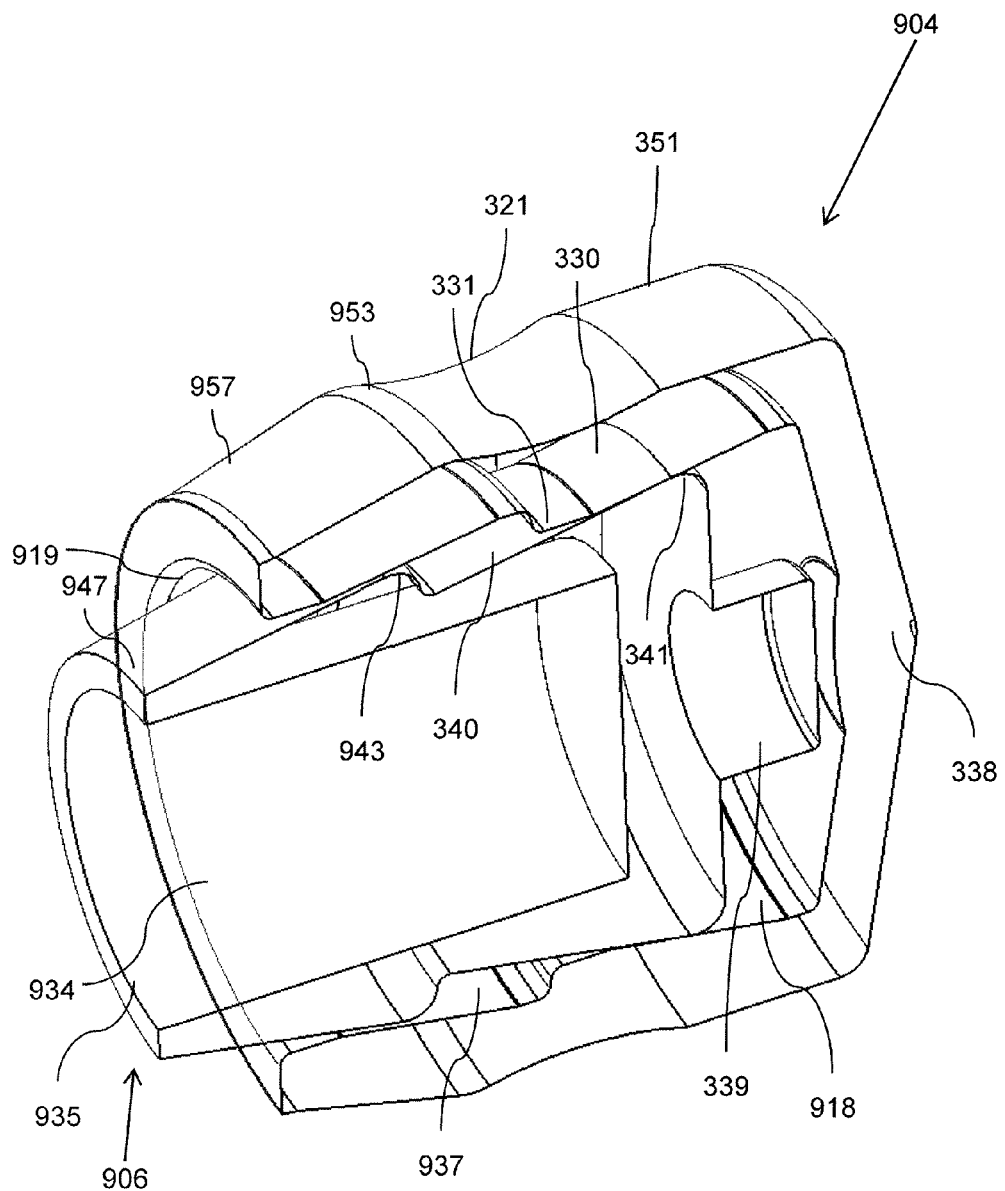
Figure 9D:
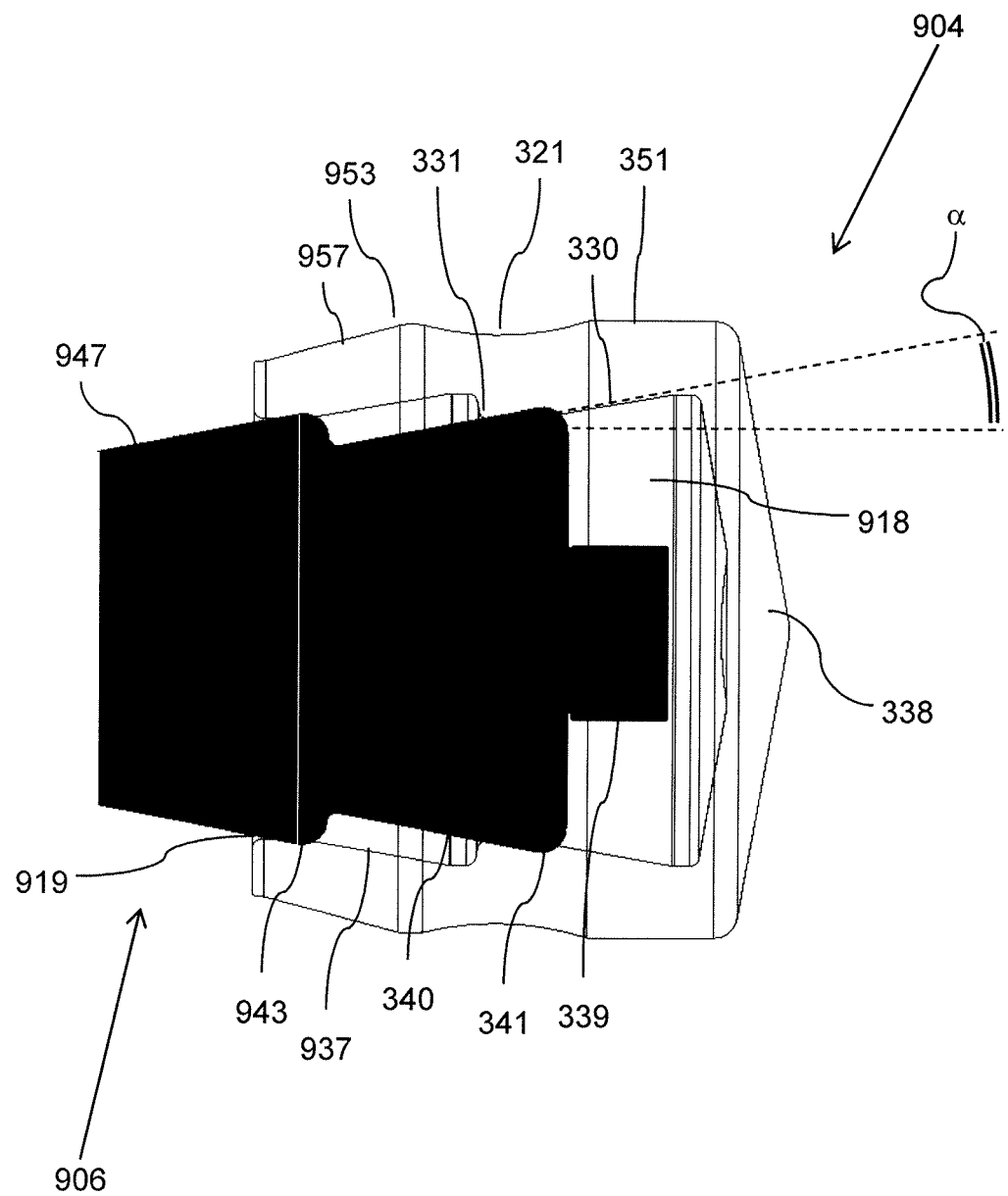
Figure 9E:
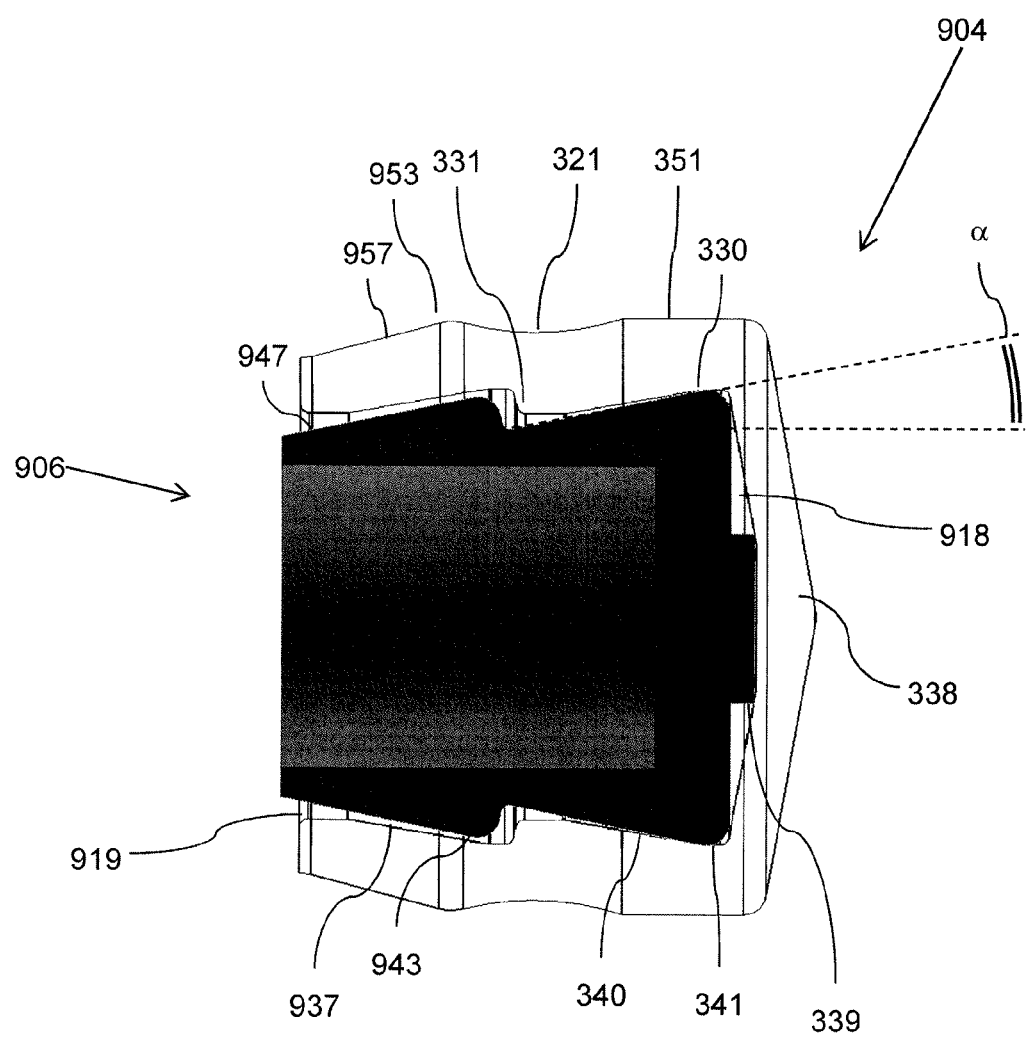
Figure 10A:
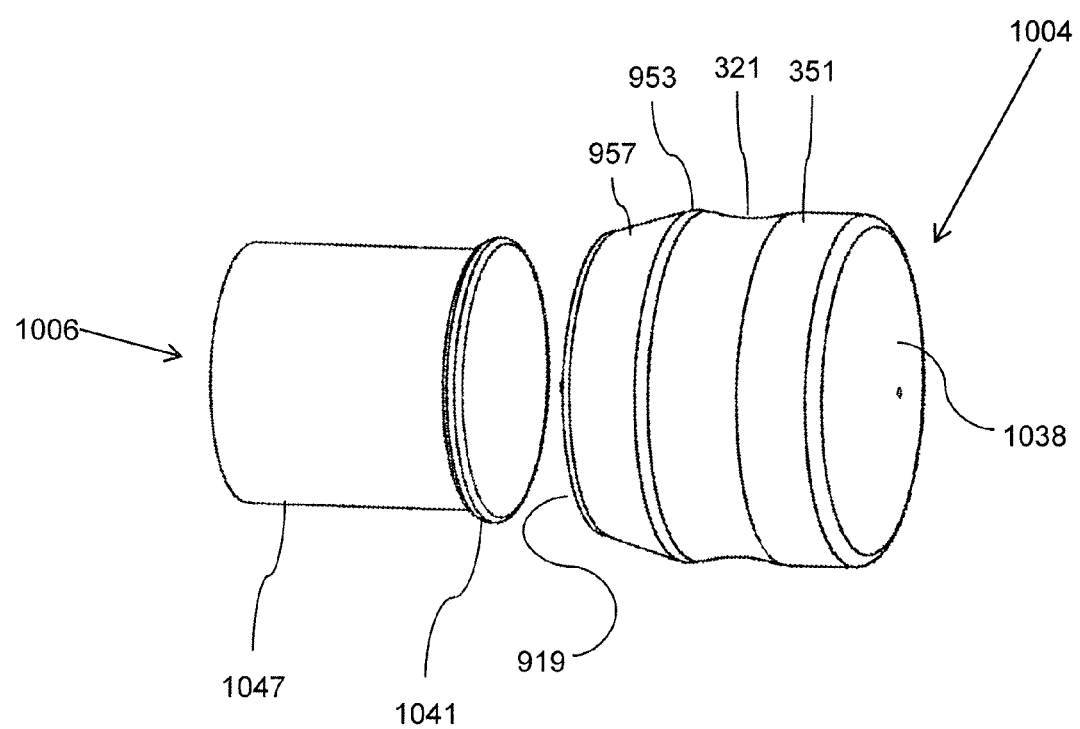
Figure 10B:
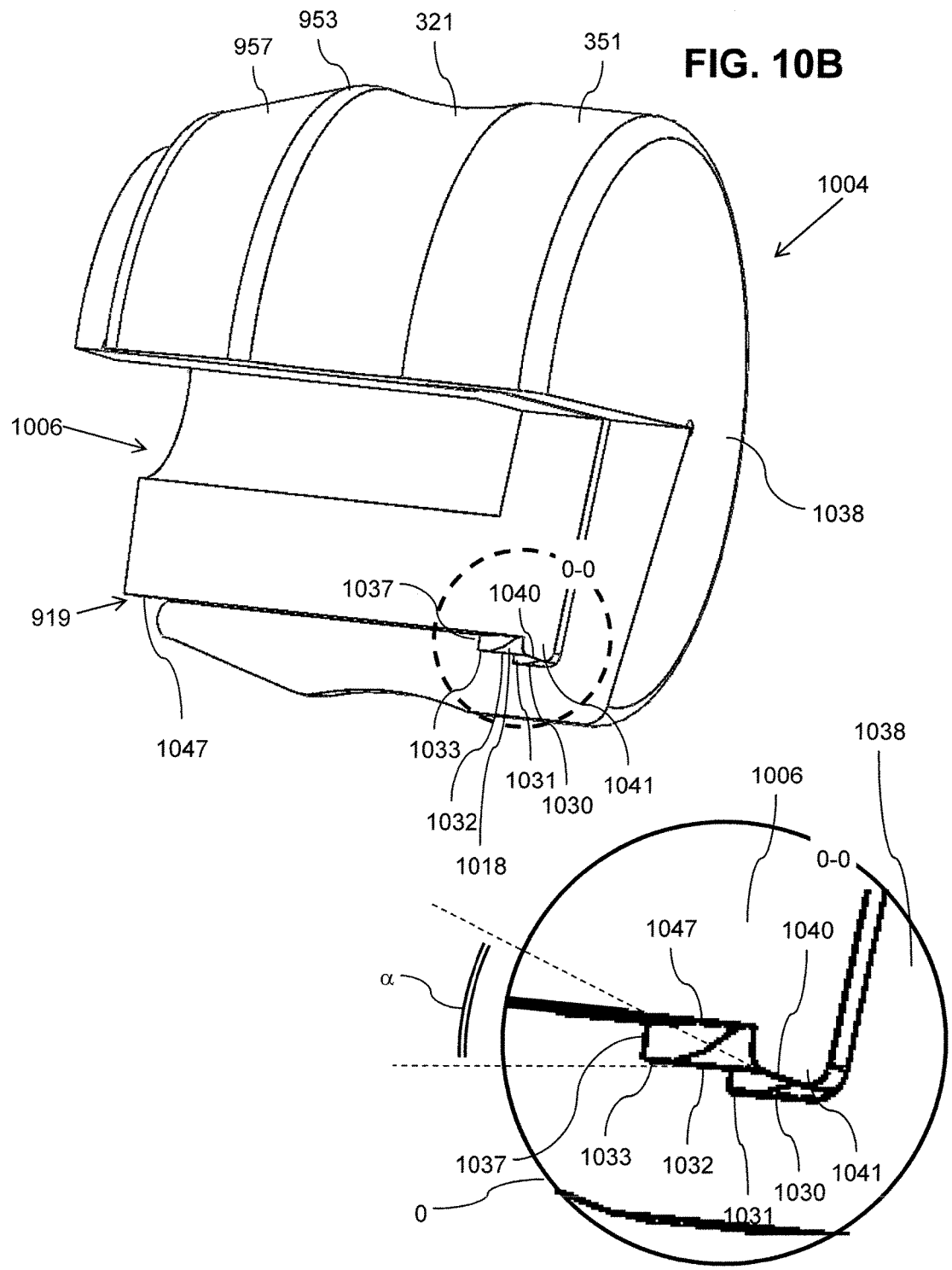

FIGS. 3A-B are cut away illustrations of a two part plunger seal biased to the parked state in accordance with an embodiment of the current invention;

FIG. 4 is a state diagram of a plunger in accordance with an embodiment of the current invention;

FIG. 5A is a flow chart illustration of a method of sealing a prefilled reservoir under vacuum in accordance with an embodiment of the current invention;

FIG. 5B is a flow chart illustration of a method of sealing a prefilled reservoir under positive pressure in accordance with an embodiment of the current invention;

FIG. 6 is a block diagram of a two part plunger system in accordance with an embodiment of the current invention;

FIG. 7 is a more detailed block diagram of a two part plunger system in accordance with an embodiment of the current invention;

FIGS. 8A-B are a cut away views of a two part plunger system in accordance with embodiments of the current invention;

FIGS. 9A-E are various views of a two part multi chamber plunger biased to the parked state in accordance with an embodiment of the current invention; and FIGS. 10A-C are various views of a two part unbiased multi chamber plunger in accordance with an embodiment of the current invention.

DESCRIPTION OF SPECIFIC EMBODIMENTS OF THE INVENTION

The present invention, in some embodiments thereof, relates to a plunger seal for a medicine cartridge (e.g. a syringe) and, more particularly, but not exclusively, to a plunger seal with adjustable sealing force against an inner wall of the syringe.

Overview

An aspect of some embodiments of the present invention relates to an adjustable plunger seal for a drug cartridge. Optionally, the seal may have a parked state and/or a mobile state and/or a contracted state. For example in the parked state the seal may tightly plug a proximal opening of a cylindrical bore containing the medicine. Optionally, in the mobile state and/or the contracted state the seal may fit less tightly into the bore facilitating insertion of the plunger into the bore and/or advance of the plunger.

In some embodiments, the plunger seal may have a coating (for example be laminated by the coating). For example, the coating may have a low reactivity and/or may protect the medicine during storage from contact with the relatively reactive body of the seal. In some embodiments, the coating may be less elastic than the body of the seal. For example, the coated seal may have reduced deformability than the seal without the coating. Optionally, the plunger may switch between the parked state and the narrow, mobile and/or contracted state without overstressing and/or damaging the coating. In some embodiments, the coating may include a tetrafluoroethylene resin film and/or ultra-high molecular weight polyethylene film having an average roughness Ra on the central line of the surface in a range of at most 0.05 µm and a kinematic friction coefficient of at most 0.2. Optionally, a plunger seal and/or a coating may include graphene.

In some embodiments, with the plunger in the parked state, the bore may be tightly sealed, for example for long term storage. Optionally, the plunger may be stable in the parked state. Alternatively or additionally, an outside force may be supplied to keep the plunger in the parked state.

In some embodiments, in the mobile state the plunger may moveably seal the reservoir. For example, in the mobile state, the plunger may be pushed distally into the bore to discharge the medicine through a distal opening of the bore. In some embodiments, the plunger may be stable in the mobile state. Alternatively or additionally, the plunger may be biased to the parked state and/or automatically revert from the mobile state to the parked state. For example, a distal force on the plunger may switch the plunger from the parked state to the mobile state and/or preserve the plunger in a mobile state.

In some embodiment, the plunger may have contracted state. Optionally in the contracted state the plunger may movably seal the bore. Alternatively or additionally, in the contracted state the plunger may fit loosely into the bore, for example allowing gas to escape in a space between an outer wall of the plunger and an inner wall of the bore.

An aspect of some embodiments of the current invention relates to a method of sealing a prefilled drug container. In some embodiments, a plunger is inserted into the container in a mobile and/or contracted state until it reaches a sealing position.

Optionally, in the sealing position, the plunger is switched to a parked state for enhanced sealing and/or storage of the drug.

In some embodiments the container may include a syringe and/or a cartridge with a cylindrical bore and/or a proximal opening. For example, the drug may be stored in a distal portion of the bore. Optionally, the plunger is inserted through the proximal opening until it reaches the drug and then expanded to seal the distal portion of the bore with the medicine.

In some embodiments the plunger seal assembly may be inserted into the bore under vacuum. For example, under vacuum, a plunger may be inserted into the proximal opening to movably seal the bore. For example, pressure may then be restored outside the container, driving the plunger into the bore until it reaches the location of the drug.

In some embodiments, the plunger may be inserted into the bore under positive pressure. Optionally, as the plunger is inserted into the bore under positive pressure, gas is allowed to escape. For example the plunger may be inserted into the bore in a state that allows gas to escape.

An aspect of some embodiments of the current invention relates to a method of distributing a drug. For example the drug may be stored in a cylindrical bore of a drug cartridge. A plunger seal system may be inserted into a proximal opening of the bore. The proximal opening of the bore may be sealed by the plunger seal. The seal may be strengthened (for example to prevent leakage, for example leakage under long term storage and/or leakage under changes in pressure and/or temperature) by increasing a normal force between the outer wall of the plunger seal and an inner wall of the bore. The drug may be metered out of the cartridge by applying a distal force to the plunger seal system. The distal force optionally reduces the normal force between the walls of the bore and the seal system and/or advances the plunger seal system distally into the bore optionally discharging the drug from a distal opening of the cartridge. For example, the cartridge reservoir may fit into a syringe fitting of a standard prefilled syringe filling machine and/or the plunger seal may be inserted into the reservoir with standard syringe plunger placing machine.

An aspect of some embodiments of the current invention relates to a plunger seal having that is put into a parked and/or enhanced sealing state by compression. In some embodiments, the seal may be compressed between two surfaces and/or with opposing forces. For example, a syringe seal may include a cavity. In the parked state, a radial outward force is optionally applied to the inner walls of the cavity. A portion of the plunger seal is compressed between the inward force on the inner walls of the cavity and the outward force on the outer surface of the plunger seal. For example, there may be radially outward pressure on the inner walls of the cavity. The pressure optionally passes to the outer surface of the seal increasing the normal force between the inner surface of the reservoir and a sealing region on the outer surface of the seal. Increasing the normal force optionally switches the seal to a parked state and/or enhances the sealing of the cartridge, for example for storage.

In some embodiments compression forces may be applied in any direction. For example, a plunger seal may act as a fluid transmitting pressure in all directions. Compressing the plunger seal in any direction optionally serves to increase the pressure on all directions all over the seal. For example, a plunger seal may have a low compressibility. Optionally compression of the plunger seal causes a great increase in pressure between the seal and the walls of the reservoir with small and/or insignificant deformation of the plunger seal. Optionally the plunger seal may be compressed in a defined space. For example, the side walls of a hollow plunger seal may be compressed in an annular space between a plunger core and a reservoir inner wall. For example, the plunger seal may be compressed between a hard cylindrical core plug and an inner wall of a cylindrical reservoir bore. Optionally compression can be by expanding the inner cavity and/or contracting the reservoir walls. Alternatively or additionally the plunger seal may be contracted longitudinally causing an over pressure laterally (for example like fluid pressure that pushes in all directions).

In some embodiments, the sealing assembly includes a plunger seal and a core. For example the plunger seal may include a cavity and/or the core may be inserted and/or wedged into the cavity. Optionally pushing the core distally into the cavity may switch the system into the mobile state.

In some embodiment, the plunger may biased to the parked state. Optionally at rest the core is pushed proximally into the sealed configuration. For example the proximal force may be supplied by elastic forces between the core and the seal.

Alternatively or additionally, the plunger may be stable in the mobile state. For example, the plunger seal and core may be actively switched from the mobile state to the parked state. For example, the plunger may be switched from the mobile state into the parked state by pulling back (proximally) on the core.

In some embodiments the plunger seal and the core are inserted into the cartridge bore together, for example in the mobile state. Alternatively or additionally, the plunger seal may be inserted into the cartridge bore in a contracted state, for example without the core. Optionally, the plunger is switched to the mobile and/or after the plunger seal has been inserted into the cartridge bore. For example, the plunger may be switched from the contracted state to the mobile and/or parked state by inserting the core into the cavity of the plunger seal.

Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Storing and Distributing a Drug

Figure 1:
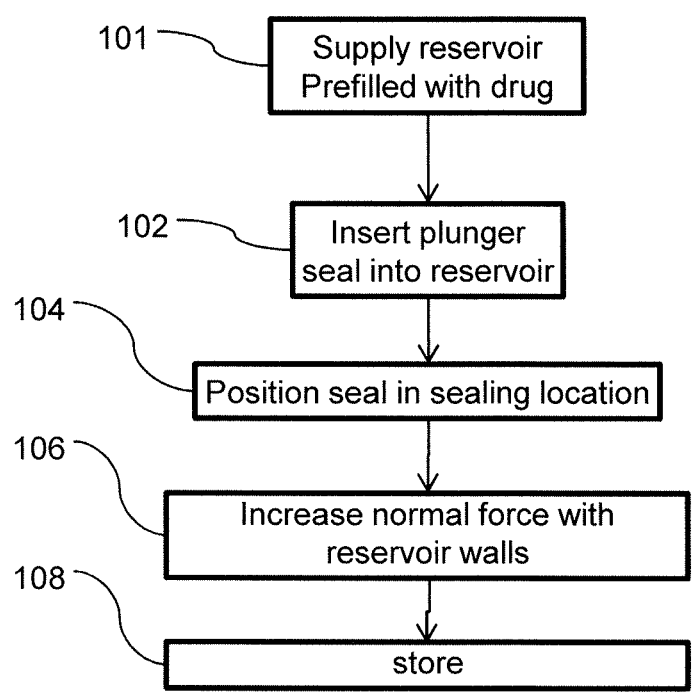

FIG. 1 is a flow chart illustration of a method of storing a drug in accordance with an embodiment of the current invention. In some embodiments, a reservoir is supplied 101 with a drug inside. Optionally, a plunger seal is inserted 102 into an opening of the reservoir and/or positioned 104 in a sealing location between the drug and the opening of the reservoir. Once in place, the plunger seal is optionally swollen radially to increase a normal force 106 and/or to seal against the inner walls of the reservoir. For example, the normal force may be increased by compressing the plunger seal. For example, the walls of the plunger seal may be compressed between two hard surfaces, for example an inner core and/or the walls of the reservoir bore. In some embodiments, the drugs may be stored 108 in the sealed reservoir.

In some embodiments the reservoir may have a cylindrical bore with a proximal opening. For example the bore and/or the plunger seal may have a circular cross section. In some embodiments, the bore may include a proximal opening and/or a distal opening, for example similar to a syringe. For example the proximal opening may be the full width of the bore. For example the distal opening may be smaller than the width of the bore. Optionally the distal opening may include a needle and/or a needle mount.

In some embodiments, the plunger seal and/or the inner walls of the reservoir may be made of and/or coated with a non-reactive coating. Optionally the non-reactive coating may limit the flexibility of the plunger seal. Optionally the unstressed plunger seal fits snugly into the bore of the reservoir. For example, when the plunger seal swells to increase pressure 106, the snug fitting walls of the bore may put significant sealing force on the plunger seal with limited deformation of the seal. The non-reactive surfaces and/or the tight seal are optionally fitting for long term storage of medicine.

FIG. 2 is a flow chart illustration of a method of discharging a drug from a cartridge in accordance with an embodiment of the current invention. In some embodiments a plunger seal may serve as a piston for discharging a fluid from the reservoir. For example, the reservoir may be stored 108 with a plunger seal swollen and/or sealed between a proximal opening of the reservoir and the drug. The normal force between the seal and the inner walls of the reservoir may be reduced 210, for example to facilitate movement of the plunger seal. Optionally, the plunger seal may be advanced 216 distally into the bore of the cartridge discharging 217 the drug. For example the drug may be discharged out of a distal opening of the reservoir. For example, advancing 216 the seal and/or discharging 217 the drug may be after reducing 210 the normal force between the plunger seal and the inner wall of the reservoir.

In some embodiments, a reservoir may be filled and/or sealed and/or stored 108 as described herein above with respect to FIG. 1. Optionally, during storage 108 the plunger seal may be sealed between the drug and the proximal opening of the reservoir bore. Optionally the distal opening may also be sealed, for example by a needle cap and/or a septum. Optionally before discharge of the drug, the distal seal may be removed and/or punctured.

In some embodiments, a plunger driver may be inserted into the proximal opening of the reservoir. For example, the plunger driver may include a rod and/or a threaded element. For example, the reservoir may be included in a cartridge of a drug delivery device and the device may insert the driver into the proximal opening of the cartridge. Optionally the plunger driver may be advanced 214 distally in the bore until it contacts the plunger seal and/or the core.

In some embodiments, pressure between the plunger seal and the wall of the reservoir may be reduced 210, for example to facilitate mobility of the plunger seal. For example, contact and/or force between the plunger driver and the plunger seal assembly may cause a reduction of the normal force between the plunger seal and the inner wall of the reservoir. Optionally the plunger driver may apply a distally directed force to the proximal side of the plunger seal assembly. Optionally after reducing the normal force between the plunger seal and the wall of the reservoir, the plunger seal still seals against the inside walls to the reservoir and/or still prevents a significant and/or fast leak of the drug past the plunger seal. Optionally, in the mobile state the plunger seal may act as a piston. For example, distal force on the plunger seal may advance 216 the plunger distally into the reservoir. In some embodiments, as the plunger seal advances 216 distally into the reservoir it acts as a piston, pushing the drug ahead of it and/or discharging 217 the drug out the distal opening of the reservoir.

Two Part Plunger Biased to a Parked State

FIGS. 3A-B are cut away illustrations of a two part plunger biased to the parked state in accordance with an embodiment of the current invention. Optionally the multi part plunger has at least two states: a first mobile state for example in which the plunger fits snugly into a reservoir bore but it loose enough to be moved by a plunger driver and a parked state in which the walls of the plunger seal push against the wall of the reservoir providing improved sealing and/or decreased mobility in comparison to the mobile state. Optionally the two part plunger includes an outer seal 304 and an inner core 306. Optionally core 306 fits into a cavity 318 in seal 304. For example, in the parked state (for example as illustrated in FIG. 3A) core 306 presses radially outward against the inner wall of seal 304. Additionally or alternatively, the plunger has a mobile state, (for example as illustrated in FIG. 3B) wherein radial pressure is released from core 306 against the inner wall of seal 304. Optionally, core seal 304 may be used in an empty state, for example wherein core 306 is not inserted into seal 304.

In some embodiments, core 306 may have a backward (proximal) facing slope 340 and/or cavity 318 may have a forward facing slope 330. In some embodiments, the angle of slope 340 and/or 330 with respect to the longitudinal axis of plunger seal 304 and/or core 306 may range between $\alpha=0$ to 1 and/or 1 to 3 and/or 3 to 10 and/or 10 to 30 and/or 30 to 50 degrees. The shallower the bevel, the more mechanical advantage is given to the radial normal force. For example a small proximal force on core 306 may produce a large radial outward force on the walls of cavity 318. Moving core 306 backward (proximally) inside cavity 318 optionally increases the radial normal force between core 306 and the walls of cavity 318. For example, in the parked state, core 306 is positioned rearward (proximally) with respect to seal 304. For example, in the mobile state, core 306 is moved forward (distally) with respect to seal 304. Alternatively another interference element, for example a shoulder and/or a protruding element may cause increase and/or decrease of the normal and/or radial force.

In some embodiments, the plunger may be biased to the parked state. For example, a distal head 339 of core 306 may contact an inner distal wall 338 of plunger seal 304 and/or be pushed back (proximally) into the parked position. Optionally, when core 306 is pushed distally (for example by a plunger driver), distal head 339 of core 306 may be compacted and/or distal wall 338 of plunger seal 304 may be compressed and/or distended distally allowing core 306 to move distally and/or releasing pressure between piston seal 304 and the walls of the reservoir.

Alternatively another interference element, for example a shoulder and/or a protruding element may cause forward and/or rearward biasing of the core with respect to the plunger seal. The plunger assembly of FIGS. 3A-B is biased to the parked state, meaning for example that the plunger system spontaneously reverts to the parked state from the mobile state.

In some embodiments, core 306 is inhibited from being ejected out an opening in cavity 318. For example, cavity 318 includes a proximal opening 319. Core 306 is optionally inhibited from exiting through opening 319 by interference between a shoulder 341 of core 306 and a shoulder 331 of cavity 318. Optionally, shoulder 341 is located towards the front (distal) end of core 306 and/or shoulder 331 is located toward the rear (proximal) end of cavity 318. For example, the proximal end of core 306 extends out of opening 319 in the parked state and/or when shoulders 331 and 341 meet (for example as shown in FIG. 3A). Alternatively another interference element, for example a protruding element may inhibit ejection of core 306 from cavity 318. Optionally the outer face of plunger seal 304 includes an indentation 321. For example, indentation 321 allows a limited deformation of plunger seal 304 for example upon insertion of core 306 into cavity 318.

In some embodiments piston seal 304 may be coated with a coating (for example a non-reactive coating). Optionally critical portion of the non-reactive coating may be over a distal portion of seal 304 that contacts the drug. For example, piston seal 304 may have a sealing shoulder 351, for example, sealing shoulder 351 may include an annular rib. For example, the critical portion of the coating may be distal to shoulder 351. Optionally, a portion of plunger seal 304 not in the critical portion (for example proximal to shoulder 351) may not be coated and/or may be allowed to flex and/or deform more than the critical portion of plunger seal 304 (for example distal to should 351). For example when core 306 is inserted into cavity 318 and/or moved between the parking position and/or the mobile position the proximal portion of plunger seal 304 may flex and/or deform. The deformation of the proximal portion of plunger seal 304 may be sufficient to damage a coating on the proximal portion (in embodiments where the proximal portion is coated). Optionally the portion of plunger seal 304 that contacts the drug (for example the distal portion of plunger seal 304) may be configured to deform only in ways and/or magnitudes that will not damage a coating thereof.

States of a Plunger

FIG. 4 is a state diagram of a plunger in accordance with an embodiment of the current invention. In some embodiments, a plunger seal may have multiple states. For example a plunger may have a contracted state 402 and/or a mobile state 406 and/or a parked state 416. Optionally in all of the states a deformation of the surface of the plunger is small enough to avoid cracking a coating of the plunger seal.

In some embodiments in a contracted state 402 a plunger may have a width slightly smaller than a reservoir. For example, when inserted into a reservoir in the contracted state, the plunger may leave space for gas to escape. Alternatively or additionally, in the contracted state the plunger may seal the reservoir. For example in the contracted state the plunger may move in the reservoir.

In some embodiments, in the mobile state a plunger may seal a reservoir.

Optionally the plunger may fit loosely enough to allow movement of the plunger, for example to discharge a drug from the reservoir.

In some embodiments in a parked state a plunger may seal a reservoir tightly. For example in the parked state the plunger seal may be tight enough for long term medicine storage. For example, the plunger may remain sealed under changes of pressure and/or temperature and/or shock. For example the seal may conform to standards of medicine packaging for example for prefilled syringes.

In some embodiments, a plunger may include a plunger seal and a core.

Optionally in the parked state, the core is positioned in a cavity of the plunger seal to exert a radial outwards force increasing a normal force between the plunger seal and the inner wall of a reservoir. Optionally, in the mobile state the core is inserted into the plunger seal in a position that produces less outward force.

Optionally, in the contracted state the core is removed from the cavity of the plunger seal.

Methods of Filling a Reservoir

FIG. 5A is a flow chart illustration of a method of sealing a prefilled reservoir in accordance with an embodiment of the current invention. In some embodiments, a reservoir may be filled under vacuum. In some embodiments, a plunger seal in a mobile and/or contracted state may fit snugly into a cylindrical reservoir bore. The snug fit may be tight enough to seal the bore under normal and/or short term conditions. The snug fit may be loose enough to allow easy movement of the plunger seal along the axis of the bore. Alternatively or additionally the plunger may be inserted in a mobile state.

In some embodiments, a reservoir is supplied 501 prefilled with a drug. For example the drug may be contained in the distal side of a bore of the reservoir.

Optionally the distal end of the bore may be sealed. Optionally the proximal end of the bore may be open. Alternatively or additionally, the distal end of the bore may be open.

In some embodiment, the proximal end of the cartridge may be sealed under vacuum. For example, the entire assembly may be placed under vacuum. Optionally, the vacuum evacuates gas from the proximal end of the bore and/or degasses the drug in distal end of the bore. While the proximal side of the bore is evacuated from gas, the plunger seal may be inserted 502 in a mobile and/or radially contracted state into the proximal opening of the bore. Optionally after inserting the plunger seal, external pressure may be restored. External pressure may push the plunger seal and/or move 504 it distally to a sealing location. For example the sealing location may be near the proximal end of the drug filled distal section of the bore. Alternatively or additionally, the plunger seal may be pushed into position and/or moved 504 for example by a rod and/or a plunger driver. Optionally the plunger seal may be stable in the mobile and/or radially contracted state. Alternatively or additionally, a the plunger seal may be held in the mobile and/or contracted state, for example by the rod and/or driver.

In some embodiments, once the plunger seal is in place, the normal force between the plunger seal and the wall of the reservoir may be increased 106.

Optionally there may be limited or no deformation of the outer surface of the plunger seal when the normal force is increased 106.

In some embodiments, increasing 106 the normal force between the plunger seal and the reservoir may include wedging a core into the plunger seal. For example the plunger seal may be inserted 502 and/or moved 504 into a sealing location without the core and/or the core may be wedged into the plunger seal when the plunger seal is in the sealing position.

In some embodiments, the core and the plunger seal may form a two part plunger. Optionally the two part plunger may have a parked state, in with the plunger seal is expanded and/or applies increased normal force to the walls of the reservoir. For example the plunger may default to the parked state when it is not being pushed distally. Alternatively or additionally, the plunger seal may be actively put into the parked state once it is in the sealing location. For example, the core may be wedged into the parked state by pulling it proximally. In some embodiments, the core may be inserted into the plunger seal before insertion 502 of the plunger seal into the reservoir and/or before moving 504 to a sealing position. For example, during insertion 502 and/or moving 504, the plunger system (including the core and the plunger seal) may be in a mobile state. Optionally once the plunger seal is in position, the core may be set to the parked state. For example a two part plunger may include various embodiments described herein above and/or herein below. Optionally, the drug in the reservoir sealed by the plunger in a parked state may be stored 208 for intermediate and/or long periods of time. Optionally the plunger seal and/or reservoir may be made of and/or coated with non-reactive material to improve storage properties. For example, the sealed reservoir may be stored in the parked state between 1 to 24 hours and/or between 1 day to 30 days and/or between 30 days to 1 year and/or between 1 year to 5 years. Under storage the plunger system in the parked state may preserve sterility, prevent leaks and/or protect the contents of the reservoir.

FIG. 5B is a flow chart illustration of a method of sealing a prefilled reservoir in accordance with an embodiment of the current invention. In some embodiments, gas may be allowed to escape past the plunger seal as it is inserted into the reservoir. For example, gas may be allowed to escape around the plunger as it is inserted into the reservoir. Optionally, gas may escape around the plunger seal when it is in a contracted state. For example, allowing gas to escape may be useful when a reservoir may be sealed under positive pressure.

One of the problems that may occur in some embodiments while sealing a syringe, cartridge or other reservoir under positive pressure is releasing gas trapped between the drug located at the distal end of the bore and the plunger seal as it is inserted 102 into the proximal opening of the bore. In some embodiments a tube may be inserted between the plunger seal and the wall of the reservoir while the plunger seal is being positioned 104 in the reservoir to allow gas to escape. Alternately or additionally, the plunger seal may be squeezed into an insertion sleeve and then released when it is in place. In some embodiments, for example where a plunger seal has a relatively stiff and/or brittle coating (for example a non reactive coating) squeezing the plunger seal into a sleeve and/or inserting a gas escape tube may lead to large local deformation of the plunger seal and/or damage to a coating of the plunger seal.

In some embodiments, a plunger seal may be inserted 102 into a reservoir and/or moved into a sealing position in a contracted and/or mobile state. For example, in the case of a two-part plunger, the plunger seal may be inserted in an empty state. For example in the empty state there may be space between the walls of the plunger seal and the reservoir allowing 503 gas to escape as the plunger seal is inserted into the reservoir. In some embodiments, in the mobile state there may be space between the walls of the plunger seal and the reservoir allowing 503 gas to escape as the plunger seal is inserted into the reservoir. Alternatively or additionally in the mobile state, the plunger seal may seal against the walls of the reservoir. Once the plunger seal is in place the reservoir may be sealed, for example by increasing 106 the normal force between the reservoir and the walls of the reservoir. In some embodiments, expansion, contraction and/or sealing of the reservoir is optionally achieved with limited deformation of the plunger seal and/or with even deformation of the plunger seal avoiding local damage to less flexible structures (for example a non-reactive coating of the plunger seal).

Cartridge and Drug Distribution Device

FIG. 6 is a block diagram of a two part plunger system in accordance with an embodiment of the current invention. Optionally a plunger system includes a plunger seal 604 intervening between a drug 728 stored in a reservoir 610 and a proximal opening of reservoir 610. Optionally, a core 606 fits to the plunger seal. For example movement of core 606 with respect to plunger seal 604 may switch the plunger system between a mobile state, a fully enhanced parked state and/or an empty state. The position of core 606 and/or plunger seal 604 may be controlled by a driver 614.

In some embodiments, a multipart plunger system may be included in a cartridge of a drug delivery device. For example, driver 614 may include a plunger rod and/or a telescoping. Optionally, movement of driver 614 may be driven by drive system include for example a motor and/or a spring drive and/or an elastic drive and/or a pressurized gas drive and/or a gear and/or a telescoping assembly and/or a worm screw.

In some embodiments, a cartridge may include reservoir 610, plunger seal 604, core 606 and/or drug 728. For example, the cartridge may be inserted into a drug delivery device. The drug delivery device optionally includes a drive system and/or driver 614. For example, the cartridge may be inserted into the device sealed by the plunger system in a parked state. The drive system optionally advances driver 614 into a proximal opening of reservoir 610. In some embodiments, contact between driver 614 and core 606 (for example a distal pressure of driver on core 606) may switch the plunger system from a parked state to a mobile state. Further advancement of driver 614 optionally pushes plunger seal 604 in the distal direction forming a piston that discharges drug 728 out of a distal opening of the reservoir. Alternatively or additionally, driver and/or a transmission and/or a telescoping assembly may be integrated into the cartridge. For example the drug delivery device may include a transmission and/or a motor which transfers energy to the transmission of the cartridge.

FIG. 7 is a detailed block diagram of a two part plunger system in accordance with an embodiment of the current invention. In some embodiments core 606 is inserted into a cavity 718 in plunger seal 604. Optionally, plunger seal 604 has an outer coating 720 that contacts a drug 728 when seal 604 is inserted into reservoir 610. For example, seal 604 is inserted through a proximal opening 722 into a bore 724 of the reservoir. Optionally bore 724 may have a distal opening 626. Distal opening 626 is optionally sealed with a cover 709.

In some embodiments, plunger seal 604 has at least two states, a narrow-mobile state and a swelled-parked state. For example, core 606 may radially expand the inner wall of cavity 718. Optionally expanding the inner wall of cavity may swell plunger seal 604 and/or increase the normal force between plunger seal 604 and the inner wall of the reservoir 610 putting the plunger into the swelled-parked state.

Optionally core 606 may be removed from cavity 718 and/or relocated to a non-interfering position in cavity 718. For example removing and/or relocating core 606 may allow the inner wall of cavity 718 to retract radially. Radially retracting the inner walls of cavity 718 may optionally reduce the normal force between plunger seal 604 and the inner wall of reservoir 610 and/or put the plunger into the narrow and/or mobile state. Optionally, in the various states and/or transitions of the plunger, deformation of the portion of the surface of plunger seal 604 is small enough to avoid damage to coating 720.

In some embodiments, during storage, plunger seal 604 seals between the drug and the proximal opening of bore 724. For example, plunger seal 604 may seal the proximal opening 722 during storage. For example, during storage, plunger seal 604 may be kept in the parked state. Optionally, during drug discharge plunger seal may seal loosely to the wall of the reservoir, for example in the mobile state. Optionally during discharge, plunger seal 604 may serve as a piston, for example to drive the drug out distal opening 626 of reservoir 610.

In some embodiments, a core 606 is biased to the swelled-parked state.

Optionally distal pressure from driver 614 moves core 606 to the mobile position and/or switches the plunger assembly into the mobile state. Alternatively or additionally, a distal force from driver 614 drives plunger seal 604 distally into bore 724 discharging drug 728.

In some embodiments distal cover 709 may be sealed during storage. For example distal cover 709 may include a needle cover and/or a septum. Optionally, distal cover 709 is opened and/or punctured before discharge of drug 728.

FIG. 8A is a cut away view of a two part plunger system in accordance with an embodiment of the current invention. For example, a two part plunger including a plunger seal 804 and/or a core 806 is shown inserted into a reservoir 810 which includes for example a prefilled syringe. For example, the prefilled and/or sealed syringe may be inserted into a drug delivery device. Optionally, after insertion a driver 814 of the delivery device advances from outside the reservoir (for example as shown in FIG. 8A) into the reservoir.

In some embodiments, a prefilled syringe may be inserted into an injection device in a parked state (for example as illustrated in FIG. 8A). For example, the plunger is in a parked state sealing between a distal portion of the bore 824b containing a drug 828 and a proximal portion of the bore 824a including a proximal opening 822. Optionally a distal opening 826 of the syringe is sealed by a septum 809a. For example, septum 809a may be punctured by a needle when reservoir 810 is inserted into a delivery device. Alternatively or additionally, there may be a puncture mechanism that punctures septum 809a at the beginning of discharge. In some embodiments, a syringe may include a needle and/or the distal seal may include a needle cap.

In some embodiments bevels 830 and 840 on plunger seal 804 and core 806 respectively are directed backwards such that when core 806 is pushed distally with respect to plunger seal 804, core 806 wedges the walls of plunger seal 804 outward optionally compressing the walls of plunger seal 804 between core 806 and the walls of reservoir 810 and/or increasing a normal force between plunger seal 804 and the walls of reservoir 810. Optionally, a front wall 838 is an interference element forcing core 806 distally such that the plunger is biased to the parked state with increased force sealing plunger seal 804 against the walls of reservoir 810.

In some embodiments, driver 814 is advance through opening 822 into bore 824a until it reaches core 806. Driver 814 optionally puts a distal force onto core 806 driving it distally with respect to plunger seal 804 and/or placing the plunger into a mobile state. Optionally further distal force of driver 814 onto the plunger drives the plunger to discharge drug 828.

FIG. 8B is a cut away view of a two part plunger system in accordance with an embodiment of the current invention. The embodiment of FIG. 8B includes for example a prefilled syringe cartridge for a pen injector. For example, a cartridge may include an integrated transmission 842. For example, transmission 842 may include a telescoping assembly (TSA). A drive gear 844 optionally connects to a motor of the injector. Optionally the distal opening of reservoir 810 includes a needle 844 sealed by a needle cap 809b. For example, in FIG. 8B the cartridge is shown is the discharge state. For example, the plunger is in a mobile state with core 806 has been pushed by driver 814 distally with respect plunger seal 804 and/or core 806 has been removed.

Alternatively and/or additionally a self contained cartridge may include a septum and/or a needle mount at the distal opening. Optionally, a cartridge with an integral driver 814 and/or transmission 842 is inserted into the drug delivery device with an enhanced parked state (for example with the plunger system in an enhanced parked state and driver 814 located proximal to core 806). Optionally, when the injector begins to rotate gear 844, driver 814 pushes core 806 switching the plunger system into a mobile state. Optionally, further rotating of gear 844 advances the plunger and/or discharges the drug.

Two Part Multi Chamber Plunger Biased to a Parked State

FIGS. 9A-E are various views of a two part plunger in accordance with an embodiment of the current invention. In some embodiments a plunger system may include an inner core 906 and/or an outer plunger seal 904. Optionally plunger seal 904 may include a stabilizing ring 953, for example in the form of an annular rib.

Optionally plunger seal 904 may include multiple chambers (for example as illustrated in FIGS. 9A-E). Optionally the chambers may be separated by a shoulder 331.

In FIG. 9A the exemplary core 906 and plunger seal 904 are shown for example in an empty state and/or a contracted state. (for example plunger seal 904 is empty and/or separated from core 906). In some embodiments, plunger seal 904 may include a rear stabilizer ring 953. For example, when plunger seal 904 is inserted into a reservoir, stabilizer ring 953 and forward sealing shoulder 351 may keep plunger seal axially aligned with the reservoir. Optionally, plunger seal 904 includes rear section 957 behind ring 953. Optionally rear section 957 may have a backward slope.

Optionally rear section 957 helps retain core 906 inside of plunger seal 904. The proximal end of section 957 optionally forms an opening 919 to a cavity 918 in plunger seal 904. For example, cavity 918 may have multiple chambers, for example as illustrated in FIGS. 9C-9E.

In some embodiments, core 906 may include multiple sections. For example a front section may be separated from a rear section by a central shoulder 943.

Optionally, one or more of the sections has a conical form. For example, each section of core 906 is a truncated right circular cone. For example, shoulder 943 forms the base of the proximal cone and/or shoulder 341 forms the base of the distal cone. The rear section is optionally has a backward slope 947. Optionally, central shoulder 943 of core 906 is larger than the unstressed size of proximal opening 919 of plunger seal 904, for example facilitating retaining core 906 inside of plunger seal 904.

Optionally, core 906 includes a hollow 934. For example, hollow 934 has a proximal opening 935. For example, a hollow 934 may fit a distal end of a plunger driver. Optionally, core 906 may include a fitting for connecting to the plunger driver. For example, hollow 934 may be internally threaded. Alternatively or additionally core 906 may be solid.

In FIGS. 9B and 9E the exemplary plunger system is shown in a mobile state (for example core 906 is located inside plunger seal 904 in a position that puts no outward pressure and/or a smaller outward pressure than in the parked state). In the mobile state the proximal end of core 906 optionally extends a slightly out proximal opening 919. For example, in the parked state the proximal end of core 906 may extend between 0.85 to 0.95 mm and/or 0.6 to 0.85 and/or 0.3 to 0.6 and/or 0 to 0.3 and/or 0.95 to 1.1 and/or 1.1 to 2 and/or 2 to 10 mm proximally from opening 919.

Cavity 918 optionally includes an expanded section into which shoulder 341 and/or 943 fit in the mobile state. For example, each chamber of plunger seal 904 has the form of a truncated right circular cone opening distally to a distal base. When core 906 is in the mobile position, shoulders 943 and/or 341 fit into the enlarged base area of the cone.

In some embodiments, core 906 may include a spacer element which may also be an interference element. For example, core 906 includes a distal head 339 (for example as illustrated in FIG. 9E). In the mobile state an interference element of core 906 optionally exerts a distal force against plunger seal 904. For example, as illustrated in FIG. 9E, the distal end of head 339 contacts the inner face of distal wall 338 of cavity 918. Optionally, distal wall 338 exerts a proximal force against core head 339, biasing core 906 towards the parked position. For example, core head 339 may elastically compress and/or deform distal wall 338 of plunger seal 904. Elastic forces of wall 338 may push core 906 proximally towards the parked position.

Optionally the deformation of the outside (distal) face of wall 338 is small enough that it does not crack an external coating of plunger seal 904. Additionally or alternatively, head 339 of core 906 may be made of an elastic material and/or head 339 may be deformed and/or compressed. For example, the elastic restoring force of head 339 on wall 338 may push core 906 proximally towards the parked position.

Alternatively or additionally, there may be an additional biasing element between core 906 and plunger seal 904. For example, a spring may intervene between head 339 and wall 338, biasing core 906 towards the parked position.

In some embodiments, core 906 may have of a memory shape. For example, core 906 may be compressed for easy fitting when inserted into cavity 918 and then expand again to its full shape inside the cavity. Alternatively or additionally, core 906 may be compressed into a sleeve for insertion into cavity 918. Alternatively or additionally, plunger seal may expand (for example by elasticity) to allow insertion of core 906 into cavity 918.

In FIGS. 9C and 9D the exemplary plunger system is shown in a parked state.

Optionally, in the parked state, the outer walls of core 906 push radially outward against the inner walls of cavity 918. For example, outer shoulder 341 of core 906 is pushed up against inner shoulder 331 of cavity 918. Optionally the force and or the radial displacement of the inner walls of cavity 918 propagates outward. For example the stress and/or strain may propagate outward to deform the exterior of plunger seal 904. For example, plunger seal 904 may swell (radially outward and/or longitudinally). For example indentation 321 may be pushed outward. For example indentation 321 may become smaller and/or a part of the outer wall of indentation 321 may be pressed up against the inner wall of a container (for example reservoir 810).

Alternatively or additionally, a normal force may be increased between the outer walls of plunger seal 904 and an inner wall of a container (for example reservoir 810). For example the force may be increased between a container (for example reservoir 810) and sealing shoulder 351 and/or central should 943. In the parked position, conical outer side walls of core 906 and/or the conical inner side walls of cavity 918 (for example between slopes 340, 330 and/or between slopes 947 and/or 937) and/or the interference between shoulders 341 and 331 and/or the interference between shoulder 943 and opening 919 may cause a distal force on core 906. The distal force on core 906 may optionally be balanced by a proximal force on head 339 by wall 338. Optionally, the proximal force on head 339 by wall 338 biases core 906 into the parked position.

Two Part Unbiased Multi Chamber Plunger

FIGS. 10A-C are various views of a two part unbiased multi chamber plunger in accordance with an embodiment of the current invention. Optionally, a plunger has at least two states, a parked state and a mobile state. Optionally, the plunger is unbiased in that it is stable in each state (optionally the plunger system does not spontaneously revert from one state to another). In some embodiments, an interference element is positioned in a cavity of a plunger seal 1004. Repositioning of the interference element (for example an axial displacement of the interference element) changes an outward radial force on an inner wall of the cavity. For example, moving the interference element distally may decrease the outward radial force and/or switch the plunger from the parked state to the mobile state. For example, moving the interference element proximally may increase the radial force and/or switch the plunger from the parked state to the mobile state.

In some embodiments, plunger system may include a plunger seal 1004 and/or a core 1006 and/or an interference element 1041. For example, element 1041 protrudes radially from core 1006. For example, as illustrated in FIG. 10B, in a mobile state, interference element 1041 may fit into a wide chamber 1030 of a cavity 1018 of a plunger seal 1004. Optionally, when core 1006 is moved proximally with respect to plunger seal 1004, the plunger system enters a parked state. In the parked state, interference element 1041 is moved into a narrower chamber 1032 of cavity 1018. In the parked state (for example as illustrated in FIG. 10C), pressure of interference element 1041 against an inner wall of narrow chamber 1032 optionally compresses the wall of the plunger seal between core 1006 and wall 1010 of the reservoir and/or increases a normal force between a sealing region 351 of the outer surface of plunger seal 1004 and an inner wall 1010 of the reservoir.

FIG. 10B illustrates a plunger assembly in a mobile state in accordance with some embodiments of the present invention. A region 0-0 of interaction between interference element 1041 and plunger seal 1004 is shown the expanded view 0. In the mobile state interference element 1041 is optionally positioned in a wide chamber 1030. Optionally, the diameter of interference element 1041 may be less than the diameter of wide chamber 1030. For example there may be a clearance between an outer wall 1040 of interference element 1041 and an inner wall 1031 of wide chamber 1030. Optionally or alternatively, outer wall 1040 of interference element 1041 may contact inner wall 1031 of wide chamber 1030 in the mobile state. In some embodiments a front wall 1038 of plunger seal and/or a portion of the outer side wall of the plunger seal distal to and/or including sealing region 351 may contact medicine when inserted into a reservoir. Optionally, front wall 1038 of plunger seal and/or a portion of the outer side wall of the plunger seal distal to and/or including sealing region 351 may be coated with a non-reactive coating. In some embodiments the non-reactive coating may have lower elasticity and/or lower flexibility than other portions of plunger seal 1004.

In some embodiments, narrow chamber 1032 may have a diameter that is less than the diameter of wide chamber 1030 by an amount ranging between 0.2 to 0.8 mm. For example interference element 1041 may protrude a distance between 0.1 to 0.4 mm from a proximal wall 1047 of core 1006. Optionally outer wall 1040 and/or proximal wall 1047 may be angled with respect to the axis of core 1006. Optionally the maximum width of interference element may between 0.2 to 0.8 mm greater than a width of a distal end of proximal wall 1047 and/or where proximal wall 1047 meets interference element 1041.

In some embodiments, the longitudinal movement of the core 1006 between the parked and mobile states may be than 1 mm and/or may range between 1 to 4 mm and/or between 4 to 7 mm and/or between 7 to 15 mm. Optionally the Optionally the angle of wedging α is adjusted to control the force of retraction used to switch the system from the mobile state to a parked state. For example, the force of retraction used to switch the system from the mobile state to a parked state may range between 10 to 100 g and/or between 100 and 200 g and/or between 200 to 500. Optionally the angle of attack α may range between 0 to 20 degrees and/or between 20 to 45 degrees and/or between 45 to 90 degrees. For example, greater angle of attack may α be associated with a greater for of retraction and/or a flatter angle of attack may be associated with a smaller force of retraction to switch the plunger to a parked state.

FIG. 10C illustrates a plunger system in a parked state in accordance with an embodiment of the current invention. A region 00-00 of interaction between interference element 1041 and the plunger seal 1004 is shown the expanded view 00. In the parked state interference element 1041 may be retracted into narrow chamber 1032. Optionally interference element 1041 pushes radially outward against an inner wall 1033 of narrow chamber 1032. For example, inner wall 1033 may be situated opposing sealing region 351 on the outer surface of plunger seal 1004. A step 1037 may impede further proximal movement of interference element 1041 from the parked state. Optionally, wall 1033 may be tipped backward retaining interference element 1041 in the parked state until a distal force switches it into the mobile state.

Optional Features

The following optional features are to be understood to be applicable to any of the embodiments described above.

In some embodiments, in the mobile state, the outward force and/or the normal force may be reduced with respect to the parked state. Reducing the normal force may facilitate movement of the seal in the bore. In some embodiments the ratio between the parked state and the mobile state of the maximum and/or average normal force between the inner wall of the reservoir and a sealing surface on the outer surface of the plunger seal may range for example between 1.1 to 1.5 and/or 1.5 to 2.5 and/or 2.5 to 5 and/or more. In some embodiments resistance to longitudinal movement of the plunger seal with respect to the cartridge due to friction between the sealing region and the inner wall of the cartridge may increase from the mobile state to the parked state in a range for example between less than 5% and/or between 5% to 30% and/or between 30% to 50% (a ratio friction between the parked and mobile states of between 1.3 to 1.5) and/or between 50% to 150% (a ratio friction between the parked and mobile states of between 1.5 to 2.5) and/or between 150% to 400% (a ratio friction between the parked and mobile states of between 2.5 to 5) and/or more. For example, the increased resistance may be between a sealing region on an outer surface of the plunger seal and the inner wall of the reservoir. For example, the sealing region may be a continuous region of contact between the outer surface of the plunger seal and an inner surface of the reservoir that divides between a sterile region of the reservoir containing a clinically significant volume of a drug and a region that does not contain a sterile clinically significant volume of the drug.

In some embodiments during storage, a core may be inserted and/or wedged into the cavity of the seal to produce the outward force. The walls of the plunger seal are optionally squeezed between the core and the inner wall of the reservoir. For example the walls of the seal may be compressed between the core and the walls of the reservoir to a thickness ranging between 75% to 85% and/or between 60 to 75% and/or between 85 to 95% and/or between 95 to 99% their unstressed thickness. The unstressed side wall thickness of the seal may for example range between 0.1 to 1 mm and/or between 1 to 1.3 mm and/or between 1.3 to 1.42 mm and/or between 1.42 to 1.48 mm and/or between 1.48 to 1.6 mm and/or between 1.6 to 2.3 mm and/or between 2.3 to 3 mm and/or between 3 to 5 mm. The thickness of the distal wall of the seal and/or the core may range for example between 0 to 1 mm and/or between 1 to 1.5 mm and/or between 1.5 to 2 mm and/or between 2 to 3 mm and/or between 3 to 5 mm. The length of the plunger seal and/or the core may range between 1 to 5 mm and/or between 5 to 10 mm and/or between 10 to 20 mm and/or between 20 to 50 mm and/or between 50 to 100 mm and/or between 100 to 200 mm and/or between 200 to 500 mm. Optionally the core is inserted into a proximal opening of the cavity.

Optionally, the core and the seal fit entirely into the bore of the reservoir.

In some embodiments, in the parked state, the core may apply an outward force to an inner wall of the seal in a region opposite the sealing region on the outer surface. Alternatively or additionally, the core may apply the force within 1 mm of a region opposite sealing region and/or between 1 mm to 5 mm and/or between 5 mm to 10 mm of the region opposite the sealing region.

In some embodiments, the seal may have an unstressed outer width that ranges between 102 and 103% the inner width of the reservoir and/or between 103 to 104% and/or between 100 to 100.5% and/or between 100.5 to 101% and/or between 101 to 102 and/or between 102 to 103 and/or between 103 to 104 and/or between 104 to 110% and/or between 99.8 to 100% and/or between 99.5 to 99.8% and/or between 95 to 99.5% and/or between 80 to 95% of the inner width of the reservoir. For example the local stretching and/or compression of the surface of the seal may range between 0 to 0.5% and/or between 0.5 to 1% and/or between 1 to 2% and/or between 2 to 3% and/or between 3 to 4% and/or between 4 to 10%. In some embodiments, the unstressed diameter of the plunger seal may range between 0.01 and 0.15 mm greater than the inner diameter of the reservoir and/or between 0.15 and 0.25 mm and/or between 0.25 to 0.5 mm and/or between 0.5 to 1 mm greater and/or the unstressed diameter of the plunger seal may be between 0.01 mm less than the inner diameter of the reservoir to 0.01 mm greater than the inner diameter of the reservoir and/or between 0.15 to 0.01 mm less than the inner diameter of the reservoir.

In some embodiments a portion of the plunger seal that does not contact the medicine may deform more than a portion that does contact the medicine and/or may deform enough to damage a coating on the portion of the plunger that does not contact the medicine. Optionally a portion of the plunger that contacts the medicine may be coated with a first material while a portion that does not contact the medicine may be coated with another material and/or may lack a coating. Alternatively or additionally the entire outer surface of the plunger may be coated, but the portion that contacts the medicine may be inhibited from deforming to a degree that might damage the coating and/or a portion that does not contact the medicine may be allowed to deform in a way that damages the coating. Optionally a distal portion of a plunger seal may contact the medicine and/or a proximal portion thereof may not contact the medicine.

In some embodiments, the coating is non-reactive. For example the coating may be compliant against United States Food and Drug Administration (FDA) Code of Federal Regulations (CFR) 21 (for example subsection 175.300 of section 175 and/or subsection 177.1550) and/or European Council (EC) directives and/or regulations for example (EC) 2023/2006 and/or (EC) 1935/2004 and/or (EC) 1272/2008. Optionally the coating is non-oxidizing. Optionally, the coating is dense and/or nonporous for example to prevent growth of mold and/or bacteria. For example the coating may produce little or no residual when exposed to water and/or heptanes and/or alcohol (for example 8%) for between 1 to 24 and/or 24 to 150 hours at temperature between −20 to 50 degrees C. and/or between 50 to 100 degrees C. and/or between 100 to 200 degrees C. at normal and/or high pressure. For example residuals may be less than 150 parts per million (ppm) and/or less than 50 ppm and/or less than 2 ppm.

In some embodiments, the core is reversed wedged into the bore. For example, a surface of the core may be tilted rearward with respect to a contact surface on the inner wall of the seal cavity, such that a proximal (rearward) force on the core produces an outward force on the inner walls of the cavity. Optionally, at rest, an interference element (for example the distal inner wall of the seal cavity) applies a proximal force to the core. In some embodiments, a plunger rod connects to the core. For example, advancing the plunger rod distally may push the core distally into the plunger seal and/or cause the plunger to switch to the mobile state and/or reduce the normal force between the plunger seal and the walls of the reservoir and/or facilitate movement of the plunger seal in the reservoir.

Optionally the wedging angle between the core and the inner wall of the cavity of the seal ranges between 0 to 8 degrees and/or 8 to 12 degrees and/or 12 to 20 degrees and/or 20 to 45 degrees.

In some embodiments, the cartridge seal is suitable for long term storage of a drug and/or discharge of the drug in a preloaded medical device. Optionally, the seal is coated with a low reactivity surface, for example protecting the drug from contamination. In some embodiments, the outer surface of the seal has reduced deformation, for example to preventing cracking of the low reactivity surface.

Optionally, the plunger seal can be inserted into the cartridge using standard syringe filling equipment. Optionally in the parked state the seal hermetically closes the proximal opening of the cartridge, for example for long term aseptic storage.

Optionally, in the mobile state, the plunger seal is easily and/or reliably movable by plunger rod, for example facilitating automated discharge of the drug.

Optionally the plunger seal and/or the core fit into the bore of the reservoir facilitating insertion into a drug delivery device and/or saving space.

A plunger seal as described herein optionally includes a gasket, a stopper, a cover, a plunger head, a bulb, a plunger tip, a plug, and/or a piston. In some embodiments a plunger (for example including a plunger seal and/or a core) may contact and/or attach to a plunger rod and/or a driver. For example the rod and/or driver may fit into a hollow in the plunger and/or be attached to the plunger by a friction fit and/or a threaded attachment and/or a snap fitting and/or a tab fitting and/or a hub and/or a bayonet fitting etc.

Optionally, in the parked state the plunger system may have improved sealing performance over the mobile state. For example, in the parked state, the reservoir may pass sterility testing and/or container and closure system integrity (CCI) standards for prefilled syringes of the FDA and/or EC. For example the system may pass CCI testing such as high voltage leak detection (HVLD), vacuum/pressure decay, mass extraction, and tracer gas detection (helium, oxygen etc.). For example some standards with which the reservoir may comply are described in Guidance for Industry Container and Closure System Integrity Testing in Lieu of Sterility Testing as a Component of the Stability Protocol for Sterile Products 2008 available from: Office of Communication, Training and Manufacturers Assistance, HFM-40 Center for Biologics Evaluation and Research Food and Drug Administration 1401 Rockville Pike, Suite 200N, Rockville, Md. 20852-1448. For example some standards with which the reservoir may comply are describe in Guidance for Industry Stability Testing of Drug Substances and Drug Products DRAFT GUIDANCE 1998 available from Office of Training and Communications, Division of Communications Management, Drug Information Branch, HFD-210, 5600 Fishers Lane, Rockville, Md.

In some embodiments, a plunger may be stable in a mobile state. For example, the plunger may remain in the mobile state until it is switched from the mobile to a parked state by an external force. For example, the plunger may be switched from the mobile to a parked state by pulling backwards (e.g. proximally) on a plunger driver and/or a plunger rod and/or a core of the plunger. For example, the seal system may be switched to the parked state by a force of between 10 to 50 grams and/or between 50 to 150 grams and/or a force between 150 to 250 grams and/or a force between 250 grams and 1 kg.

In some embodiments the plunger is switched from the parked to the mobile state by an external force. For example, applying a distal force to the seal system may switch the system into the mobile state. Optionally the seal system is switched into the mobile state by pushing distally on a plunger driver and/or a plunger rod and/or a plunger core. For example, the plunger system may be switched from the parked to the mobile state by a force of between 10 to 50 grams and/or between 50 to 100 grams and/or between 100 to 300 grams and/or between 300 g to 1 kg. Optionally, in the mobile state the drug is discharged by a distal force on the plunger system. For example the distal force for discharging the drug may be greater than the distal force for switching from the parked to the mobile state for example by between 0 to 20% and/or 20 to 40% and/or 50 to 100% and/or 100 to 200% and/or 200 to 500%.

Alternatively or additionally, the distal force for discharging the drug may be less than the distal force for switching from the parked to the mobile state for example by between 0 to 20% and/or 20 to 40% and/or 50 to 80%. For example, when the plunger is parked a distal force causes distal movement (for example of a core with respect to the plunger seal) putting the plunger into the mobiles state. Once in the mobile state, further distal force may cause the plunger to move distally for example to discharge a drug.

In some embodiments the system is switched from a parked to a mobile state and/or from mobile state to a parked state by a movement of a core and/or a plunger rod and/or a driver of between 0.1 to 1 mm and/or between 1 to 3 mm and/or between 3 to 5 mm and/or between 5 to 10 mm. For example, switching from a parked to a mobile state may include moving a core and/or a plunger rod and/or a driver distally. For example, switching from a mobile to a parked state may include moving a core and/or a plunger rod and/or a driver proximally. In some embodiments switching from a parked to a mobile state is reversible. In some embodiments switching from a mobile to a parked state is reversible.

In some embodiments, the cartridge may be stored with the drug and the plunger seal in the enhanced parked state. For example, the drug may be stored for all or part of a day and/or for between a days and a week and/or for between a week and a month and/or between a month and 4 months and/or between 4 months to a year.

Optionally, the cartridge may be inserted into a drug delivery device with the drug in the distal end of the bore and with the sealing system sealing between the drug and the proximal opening of the bore. Optionally there may be a space between the proximal opening of the bore and the proximal end of the sealing system. Optionally when the cartridge is inserted into the drug delivery device the sealing system may protrude proximally from the cartridge bore less than 2 cm. Optionally, when the cartridge is inserted into the drug delivery device the sealing system may be entirely within the bore of the cartridge. Optionally after insertion of the cartridge into the drug delivery device, a plunger rod may be advanced distally to engage the sealing system.

In some embodiment, when in a parked state, a portion of a cavity in said plunger seal may be expanded with respect to a mobile state. For example, width of the cavity may be expanded by a quantity ranging between 0.01 mm to 0.1 mm and/or between 0.1 mm to 0.6 mm and/or between 0.6 to 1.0 mm and/or between 1.0 to 2.0 mm and/or between 2 to 5 mm and/or between 5 to 10 mm in the parked state. In some embodiments, a core may include an interference element. For example the interference element may protrude from a narrow portion of the core by a distance ranging between 0.005 mm to 0.05 mm and/or between 0.05 mm to 0.3 mm and/or between 0.5 to 0.5 mm and/or between 0.5 to 1.0 mm and/or between 1 to 2.5 mm and/or between 2.5 to 5 mm. For example the interference element may be distal to the narrow portion.

Optionally the cavity of the plunger seal may have one, two, or more chambers. Optionally the core may have a uni-modal shape and/or a bi-modal shape and/or a multi-modal shape.

It is expected that during the life of a patent maturing from this application many relevant materials and/or shapes will be developed for plunger seals and the scope of the terms plunger seal and coating is intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cartridge for a drug delivery device comprising:
   a reservoir including a longitudinally oriented cylindrical bore having a proximal opening;
   a plunger seal having a sealing region on an exterior surface thereof, said sealing region sized to fit closely into said cylindrical bore; said plunger seal including a cavity; and
   a core fitting into said cavity and being movable relative to the cavity between a parked state of the plunger seal and a mobile state of the plunger seal, wherein:
      the core is shaped to apply a radially outward force against an inner wall of said cavity, in the parked state, increasing a normal force between said sealing region and an interior wall of said cylindrical bore, and wherein a distal force applied to the core advances the core forward within the cavity into the mobile state, reducing the radially outward force against the interior wall of said cavity; and
      an inner distal wall of the plunger seal abuts a distal head of the core to stabilize the core in the parked state, and at least one of an inner distal-most wall of the plunger seal and a distal-most head of the core is compressed to move the core into the mobile state.

2. The cartridge of claim 1, wherein said core includes an interference element with a distally increasing radius and wherein said cavity includes a region with distally increasing radius.

3. The cartridge of claim 1, wherein said core has a length less than 2 cm.

4. The cartridge of claim 1, wherein an unstressed outer diameter of said sealing region ranges between 99 to 103% an inner diameter of said cylindrical bore.

5. The cartridge of claim 1, wherein a maximum deformation of a diameter across said sealing region remains less than 0.5 mm.

* * * * *